United States Patent [19]

Angerbauer et al.

[11] Patent Number: 4,968,689
[45] Date of Patent: Nov. 6, 1990

[54] CERTAIN 2,6-DIISOPROPYL-4-(4-FLUORO-PHENYL)-3,5-BIS-DIMETHYL-3',5'-DIHYDROXY-HEPT-6-ENOATE-PYRIDINE DERIVATIVES USEFUL FOR TREATING LIPOPROTEINAEMIA AND ARTERIOSCLEROSIS

[75] Inventors: Rolf Angerbauer; Peter Fey; Walter Hübsch, all of Wuppertal; Thomas Philipps, Cologne; Hilmar Bischoff, Wuppertal; Dieter Petzinna, Duesseldorf; Delf Schmidt, Wuppertal, all of Fed. Rep. of Germany; Thomas Günter, Arese, Italy

[73] Assignee: Bayer Aktiengesellschaft, Leverkusen, Fed. Rep. of Germany

[21] Appl. No.: 298,453

[22] Filed: Jan. 17, 1989

[30] Foreign Application Priority Data

Jan. 20, 1988 [DE] Fed. Rep. of Germany ....... 3801440
Jul. 29, 1988 [IT] Italy ................. 21587/A88

[51] Int. Cl.$^5$ .................... C07D 213/55; A61K 31/44
[52] U.S. Cl. .................... 514/277; 546/342; 546/268; 546/284; 546/344
[58] Field of Search .......... 546/342; 514/277

[56] References Cited

U.S. PATENT DOCUMENTS 4,727,078 2/1988 Terao et al. .................. 514/277

Primary Examiner—Alan L. Rotman
Attorney, Agent, or Firm—Sprung Horn Kramer & Woods

[57] ABSTRACT

For the treatment of lipoproteinaemia and arteriosclerosis, the new disubstituted pyridines of the formula

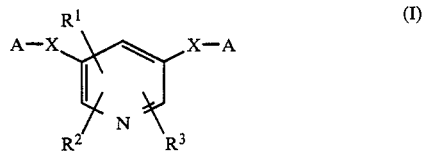

in which
$R^1$ is optionally substituted aryl or heteroaryl,
$R^2$ is cycloalkyl or optionally substituted alkyl,
$R^3$ is hydrogen, cycloalkyl, or optionally substituted alkyl, aryl or heteroaryl,
X is $-CH_2-CH_2-$ or $-CH=CH-$,
A is

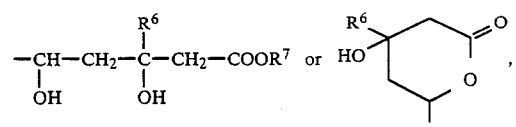

$R^6$ is hydrogen or alkyl, and
$R^7$ is hydrogen, alkyl, aralkyl or a cation.

6 Claims, No Drawings

CERTAIN 2,6-DIISOPROPYL-4-(4-FLUORO-PHENYL)-3,5-BIS-DIMETHYL-3',5'-DIHYDROXY-HEPT-6-ENOATE-PYRIDINE DERIVATIVES USEFUL FOR TREATING LIPOPROTEINAEMIA AND ARTERIOSCLEROSIS

The invention relates to disubstituted pyridines, intermediates for their preparation, and their preparation and their use in medicaments.

It has been disclosed that lactone derivatives isolated from fungal cultures are inhibitors of 3-hydroxy-3-methyl-glutaryl coenzyme A reductase (HMG-CoA reductase) [mevinolin, EP-A No. 22,478; U.S. Pat. No. 4,231,938]. Moreover, certain indole derivatives or pyrazole derivatives are also inhibitors of HMG-CoA reductase [EP-A No. 1,114,027; U.S. No. 4,613,610].

Disubstituted pyridines of the general formula (I)

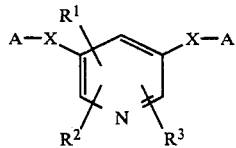

in which $R^1$ - denotes heteroaryl which can be monosubstituted, disubstituted or trisubstituted by identical or different halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^4R_5$, wherein $R^4$ and $R^5$ - are identical or different and denote alkyl, aryl, aralkyl, acyl, alkylsulphonyl or arylsulphonyl, or

- denotes aryl which can be monosubstituted to pentasubstituted by identical or different alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^4R^5$, wherein $R^4$ and $R^5$ have the abovementioned meaning, $R^2$ - denotes cycloalkyl, or

- denotes alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl or acyl, or by a group of the formula —$NR^4R^5$, wherein $R^4$ and $R^5$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the last-mentioned substituents can be monosubstituted, disubstituted or trisubstituted by identical or different halogen, cyano, trifluoromethyl, trifluoromethoxy, alkyl, alkoxy, alkylthio or alkylsulphonyl, $R^3$ - denotes hydrogen, or

- denotes cycloalkyl, or

- denotes alkyl which can be substituted by halogen, cyano, alkoxy, alkylthio, alkylsulphonyl, trifluoromethyl, trifluoromethoxy, trifluomethylthio, trifluoromethylsulphonyl, alkoxycarbonyl or acyl, or by a group of the formula —$NR^4R^5$, wherein $R^4$ and $R^5$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals can be monosubstituted, disubstituted or trisubstituted by identical or different halogen, cyano, trifluoromethyl, trifluoromethoxy, alkyl, alkoxy, alkylthio or alkylsulphonyl, or

- denotes heteroaryl which can be monosubstituted, disubstituted or trisubstituted by identical or different halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^4R^5$, wherein $R^4$ and $R^5$ have the abovementioned meaning, or

- denotes aryl which can be monosubstituted to pentasubstituted by identical or different alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^4R^5$, wherein $R^4$ and $R^5$ have the abovementioned meaning, X - denotes a group of the formula —$CH_2$—$CH_2$— or —CH=CH—, and A - denotes a group of the formula

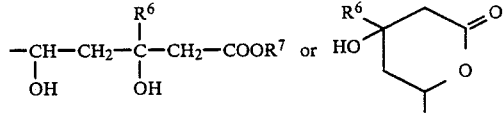

wherein $R^6$ - stands for hydrogen or alkyl and $R^7$ - stands for hydrogen or

- stands for alkyl, aryl or aralkyl or

- stands for a cation, have now been found.

Surprisingly, the disubstituted pyridines according to the invention show a superior inhibitory action on HMG-CoA reductase (3-hydroxy-3-methyl-glutaryl coenzyme A reductase).

Cycloalkyl in general stands for a cyclic hydrocarbon radical having 3 to 8 carbon atoms. The cyclopropane, cyclopentane and the cyclohexane ring is preferred. Examples which may be mentioned are cyclopropyl, cyclopentyl, cyclohexyl, cycloheptyl and cyclooctyl.

Alkyl in general stands for a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkoxy in general stands for a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy Alkylthio in general stands for a straight-chain or branched hydrocarbon radical having 1 to 12 carbon atoms which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Alkylsulphonyl in general stands for a straight-chain or branched hydrocarbon radical having 1 to 12 carbon atoms which is bonded via an $SO_2$ group. Lower alkylsulphonyl having 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentylsulphonyl, hexylsulphonyl and isohexylsulphonyl.

Sulphamoyl (aminosulphonyl) stands for the group $-SO_2-NH_2$.

Aryl in general stands for an aromatic radical having 6 to about 12 carbon atoms. Preferred aryl radicals are phenyl, naphthyl and biphenyl.

Aryloxy in general stands for an aromatic radical having 6 to about 12 carbon atoms which is bonded via an oxygen atom. Preferred aryloxy radicals are phenoxy and naphthyloxy.

Arylthio in general stands for an aromatic radical having 6 to about 12 carbon atoms which is bonded via a sulphur atom. Preferred arylthio radicals are phenylthio and naphthylthio.

Arylsulphonyl in general stands for an aromatic radical having 6 to about 12 carbon atoms which is bonded via an $SO_2$ group. Examples which may be mentioned are phenylsulphonyl, naphthylsulphonyl and biphenylsulphonyl.

Aralkyl in general stands for an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

Aralkoxy in general stands for an aralkyl radical having 7 to 14 carbon atoms, the alkylene chain being bonded via an oxygen atom. Aralkoxy radicals having 1 to 6 carbon atoms in the aliphatic moiety and 6 to 12 carbon atoms in the aromatic moiety are preferred. Examples which may be mentioned are the following aralkoxy radicals: benzyloxy, naphthylmethoxy, phenethoxy and phenylpropoxy.

Aralkylthio in general stands for an aralkyl radical having 7 to about 14 carbon atoms, the alkyl chain being bonded via a sulphur atom. Aralkylthio radicals having 1 to 6 carbon atoms in the aliphatic moiety and 6 to 12 carbon atoms in the aromatic moiety are preferred. Examples which may be mentioned are the following aralkylthio radicals: benzylthio, naphthylmethylthio, phenethylthio and phenylpropylthio.

Aralkylsulphonyl in general stands for an aralkyl radical having 7 to about 14 carbon atoms, the alkyl radical being bonded via an $SO_2$ link. Aralkylsulphonyl radicals having 1 to 6 carbon atoms in the aliphatic moiety and 6 to 12 carbon atoms in the aromatic moiety are preferred. Examples which may be mentioned are the following aralkylsulphonyl radicals: benzylsulphonyl, naphthylmethylsulphonyl, phenethylsulphonyl and phenylpropylsulphonyl.

Alkoxycarbonyl can be represented, for example, by the formula

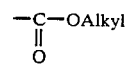

In this connection, alkyl stands for a straight-chain or branched hydrocarbon radical having 1 to 12 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl and isobutoxycarbonyl.

Acyl in general stands for phenyl or straight-chain or branched lower alkyl having 1 to about 6 carbon atoms which are bonded via a carbonyl group. Phenyl and alkyl radicals having up to 4 carbon atoms are preferred. Examples which may be mentioned are benzoyl, acetyl, ethylcarbonyl, propylcarbonyl, isopropylcarbonyl, butylcarbonyl and isobutylcarbonyl.

Halogen in general stands for fluorine, chlorine, bromine or iodine, preferably for fluorine, chlorine or bromine. Particularly preferably, halogen stands for fluorine or chlorine.

Heteroaryl in general stands for a 5- to 6-membered aromatic ring which can contain oxygen, sulphur and/or nitrogen as hetero atoms and onto which can be fused further aromatic rings. 5- and 6-membered aromatic rings which contain one oxygen, one sulphur and/or up to 2 nitrogen atoms and which are optionally fused to benzene are preferred. Heteroaryl radicals which may be mentioned as particularly preferred are thienyl, furyl, pyrolyl, pyrazolyl, pyridyl, pyrimidyl, pyrazinyl, pyridazinyl, quinolyl, isoquinolyl, quinazolyl, quinoxalyl, phthalazinyl, cinnolyl, thiazolyl, benzothiazolyl, isothiazolyl, oxazolyl, benzoxazolyl, isoxazolyl, imidazolyl, benzimidazolyl, indolyl and isoindolyl.

In the context of the present invention, disubstituted pyridines (Ia) correspond to the general formula

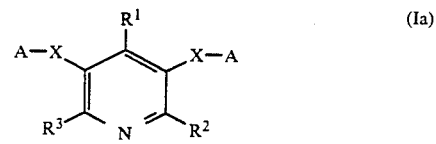

in which
$R^1$, $R^2$, $R^3$, X and A have the abovementioned meaning.

In the context of the present invention, disubstituted pyridines (Ib) correspond to the general formula

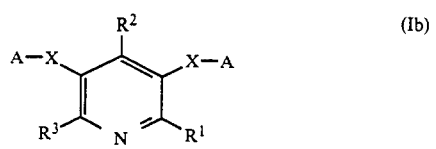

in which

R¹, R², R³, X and A have the abovementioned meaning.

In the context of the general formula (I), compounds having the general formulae (Ia) and (Ib) are preferred.

Preferred compounds are those of the general formula (Ia) and (Ib)

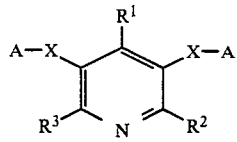
(Ia)

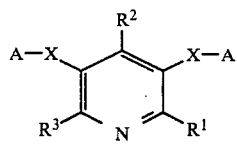
(Ib)

in which

R¹ - denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl, or

- denotes phenyl or naphthyl, each of which can be monosubstituted to tetrasubstituted by identical or different lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula —NR⁴R⁵, where R⁴ and R⁵ are identical or different and denote lower alkyl, phenyl, benzyl, acetyl, benzoyl, phenylsulphonyl or lower alkylsulphonyl, R² - denotes cyclopropyl, cyclopentyl or cyclohexyl, or

- denotes lower alkyl which can be substituted by fluorine, chlorine, bromine, cyano, lower alkoxy, lower alkylthio, lower alkylsulphonyl, phenyl, trifluoromethyl, trifluoromethoxy, trifluoromethylsulphonyl, lower alkoxycarbonyl, benzoyl or lower alkylcarbonyl, or by a group of the formula —NR⁴R⁵, wherein R⁴ and R⁵ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by identical or different fluorine, chlorine, bromine, lower alkyl, lower alkoxy, trifluoromethyl or trifluoromethoxy, R³ - denotes hydrogen, or

- cyclopropyl, cyclopentyl or cyclohexyl, or
- denotes lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl or lower alkylcarbonyl, or by a group of the formula —NR⁴R⁵, wherein R⁵ and R⁶ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by identical or different fluorine, chlorine, bromine, lower alkyl, lower alkoxy, trifluoromethyl or trifluoromethoxy,

- denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl, or

- denotes phenyl or naphthyl, each of which can be monosubstituted to tetrasubstituted by identical or different lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula —NR⁵R⁶, where R⁵ and R⁶ have the abovementioned meaning, X - denotes a group of the formula —CH=CH— and A - denotes a group of the formula

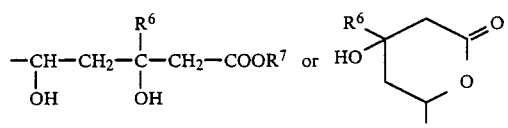

wherein

R⁶ - denotes hydrogen or lower alkyl, and

R⁷ - denotes lower alkyl, phenyl or benzyl, or

- denotes a physiologically tolerable cation.

Particularly preferred compounds are those of the general formula (Ia) and (Ib) in which R¹ - denotes pyridyl, pyrimidyl, quinolyl or isoquinolyl, each of which can be substituted by fluorine, chlorine, methyl, methoxy or trifluoromethyl, or

- denotes phenyl which can be monosubstituted, disubstituted or trisubstituted by identical or different methyl, ethyl, propyl, isopropyl, butyl, isobutyl, tert.butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl or tert.butoxycarbonyl, R² - denotes cyclopropyl, cyclopentyl or cyclohexyl, or

- denotes methyl, ethyl, propyl, isopropyl, butyl, sec.-butyl or tert.butyl, each of which can be substituted by fluorine, chlorine, bromine, cyano, methoxy, ethoxy, propoxy, isopropoxy, butoxy, sec.butoxy, tert.butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylthio, phenylsulphonyl, benzyloxy, benzylthio or benzylsulphonyl, $R^3$ - denotes hydrogen, cyclopropyl, cyclopentyl or cyclohexyl, or

- denotes methyl, ethyl, propyl, isopropyl, butyl, isobutyl, tert.butyl, pentyl, isopentyl, hexyl or isohexyl, each of which can be substituted by fluorine, chlorine, bromine, cyano, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.butoxycarbonyl, benzoyl, acetyl or ethylcarbonyl, or by a group $—NR^4R^5$, where $R^4$ and $R^5$ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, quinolyl, isoquinolyl, thienyl, furyl, phenyl, phenoxy, phenylthio, phenylsulphonyl, benzyloxy, benzylthio or benzylsulphonyl, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.butoxy, trifluoromethyl or trifluoromethoxy, or

- denotes thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzothiazolyl, where the radicals mentioned can be substituted by fluorine, chlorine, methyl, ethyl, propyl, isopropyl, butyl, isobutyl, tert.butyl, methoxy, ethoxy, propoxy, isopropoxy, butoxy, isobutoxy, tert.butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.butoxycarbonyl, or

- denotes phenyl which can be monosubstituted, disubstituted or trisubstituted by identical or different methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl or tert.butoxycarbonyl, or by a group $—NR^4R^5$, where $R^4$ and $R^5$ have the abovementioned meaning, X - denotes a group of the formula $—CH=CH—$ and A - denotes a group of the formula

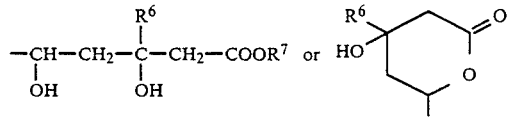

wherein $R^6$ - denotes hydrogen, methyl, ethyl, propyl, isopropyl, butyl, isobutyl or tert.butyl and $R^7$ - denotes hydrogen, methyl, ethyl, propyl, isopropyl, butyl, isobutyl, tert.butyl or benzyl, or

- denotes a sodium, potassium, calcium or magnesium or ammonium ion.

Very particularly preferred compounds are those of the general formulae (Ia) and (Ib) in which $R^1$ - denotes phenyl which can be monosubstituted or disubstituted by identical or different methyl, ethyl, propyl, isopropyl, phenoxy and/or fluorine, $R^2$ - stands for cyclopropyl or cyclohexyl or denotes methyl, ethyl, propyl, isopropyl, butyl, isobutyl or tert.butyl, each of which can be substituted by fluorine, chlorine, methoxy, phenyl or phenoxy, $R^3$ - denotes hydrogen, cyclopropyl, cyclopentyl or cyclohexyl or phenyl, or

- denotes methyl, ethyl, propyl, isopropyl, butyl or benzyl,

X - denotes a group of the formula

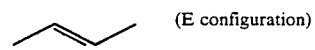 (E configuration)

and

A - denotes a group of the formula

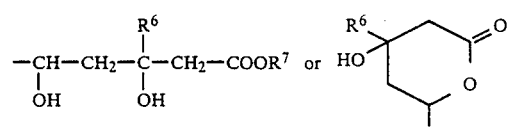

wherein $R^6$ - denotes hydrogen and and $R^7$ - denotes hydrogen, methyl or ethyl, or

- denotes a sodium or potassium cation.

The disubstituted pyridines of the general formula (I) according to the invention have several asymmetric carbon atoms and can therefore exist in various stereochemical forms. The invention relates both to the individual isomers and to their mixtures.

Depending on the meaning of the groups X or the radicals A, different stereoisomers result, which are more closely illustrated in the following:

(a) If the group —X— stands for a group of the formula $—CH=CH—$, then the compounds according to the invention can exist in two stereoisomeric forms which can have the E configuration (II) or the Z configuration (III) on the double bond:

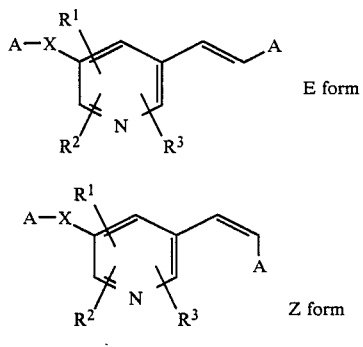

E form (II)

Z form (III)

wherein
$R^1$, $R^2$, $R^3$, X and A have the abovementioned meaning.

Preferred compounds of the general formula (I) are those having the E configuration (II).

(b) If the radical —A stands for a group of the formula

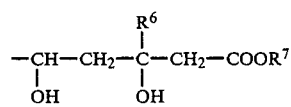

then the compounds of the general formula (I) possess at least two asymmetric carbon atoms, namely the two carbon atoms to which the hydroxyl groups are bonded. Depending on the relative position of these hydroxyl groups to one another, the compounds according to the invention can exist in the erythro configuration (IV) or in the threo configuration (V).

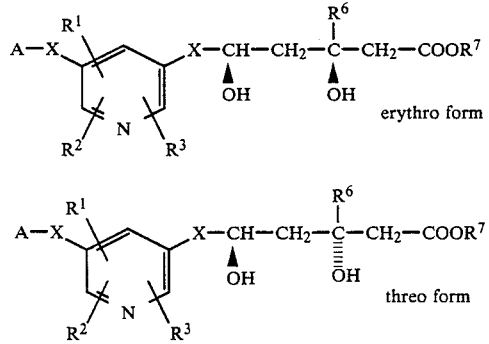

erythro form (IV)

threo form (V)

Again, two enantiomers each exist of the compounds in the erythro and in the threo configuration, namely the 3R,5S-isomer or the 3S,5R-isomer (erythro form) and also the 3R,5R-isomer and the 3S,5S-isomer (threo form).

In this connection, the erythro configuration isomers are preferred, the 3R,5S-isomers and also the 3R,5S-3S,5R-racemate being particularly preferred.

(c) If the radical —A stands for a group of the formula

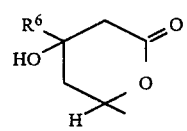

then the disubstituted pyridines possess at least two asymmetric carbon atoms, namely the carbon atom to which the hydroxyl group is bonded, and the carbon atom to which the radical of the formula

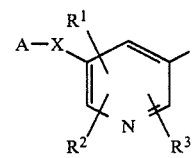

is bonded. Depending on the position of the hydroxyl group to the free valency on the lactone ring, the disubstituted pyridines can exist as the cis-lactones (VI) or as the trans-lactones (VII).

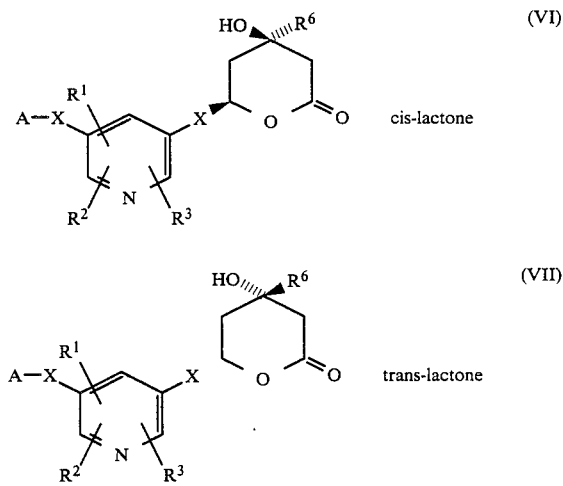

cis-lactone (VI)

trans-lactone (VII)

Again, two isomers each exist of the cis-lactone and the trans-lactone, namely the 4R,6R-isomers or the S,6S-isomers (cis-lactone), and the 4R,6S-isomers or S,6R-isomers (trans-lactone). Preferred isomers are the trans-lactones. The 4R,6S-isomers (trans) and the 4R,6S-4S,6R-racemate are particularly preferred in this case.

The following isomeric forms of the substituted pyridines may be mentioned as examples:

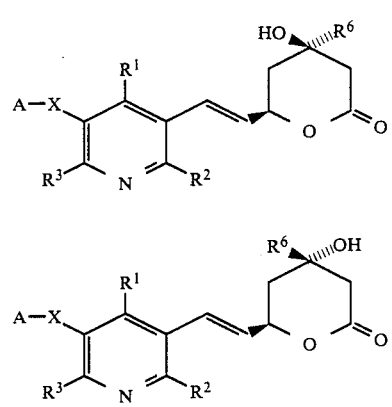

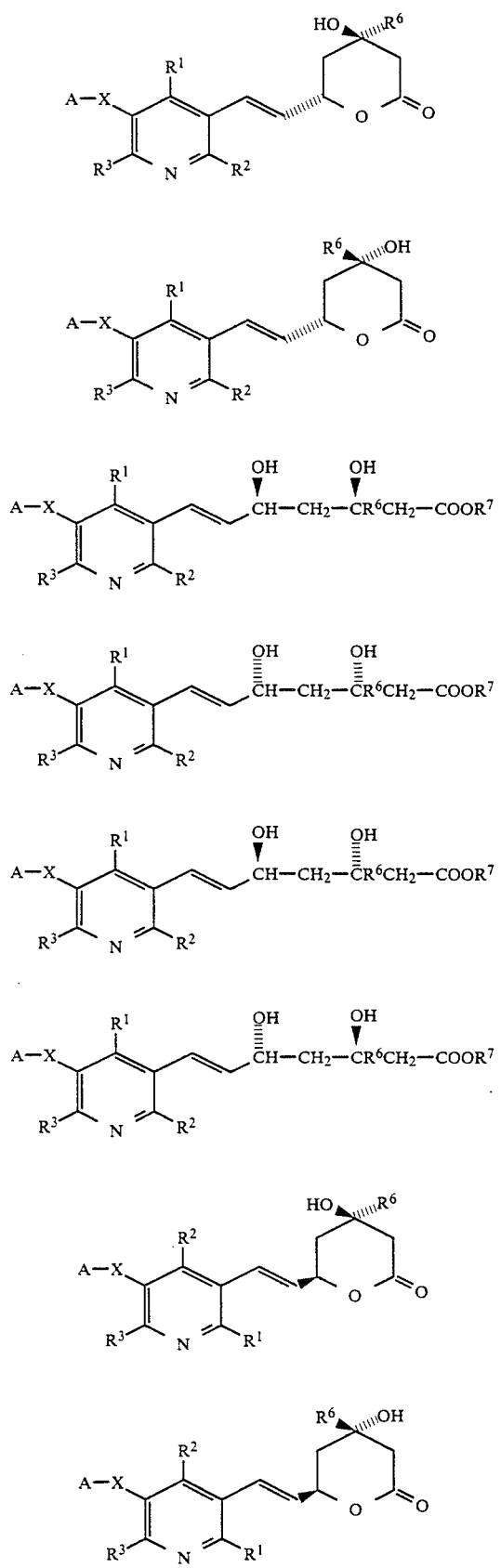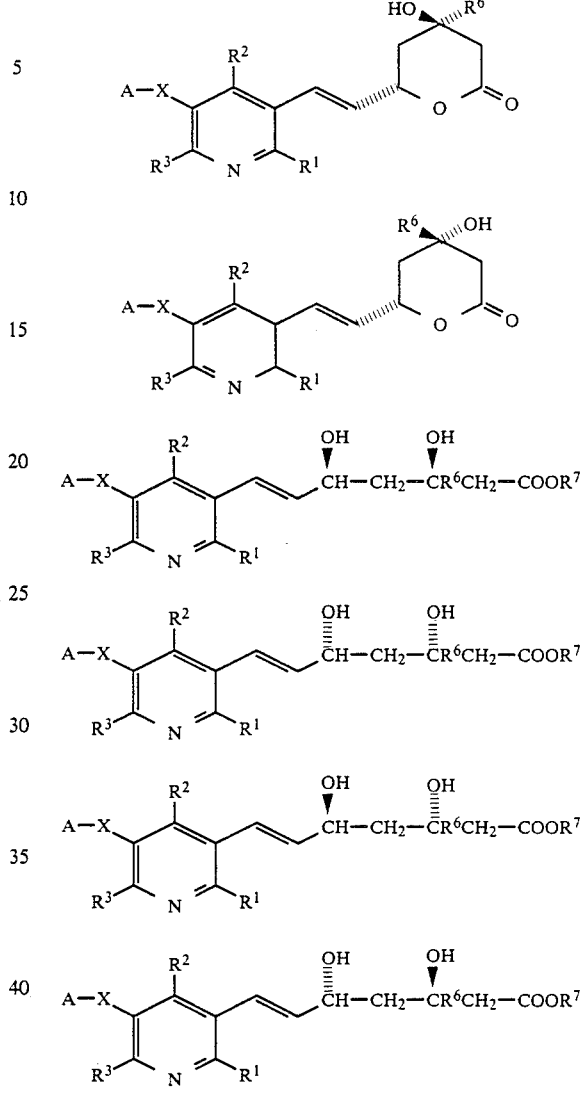

Moreover, further possibilities for isomer formation result, since the disubstituted pyridines according to the invention are substituted by two groups of the formula —X—A in the molecule. The invention likewise relates to all stereoisomers which result through the second group of the formula —X—A, in particular in connection with the first group —X—A.

In addition, a process for the preparation of the disubstituted pyridines of the general formula (I)

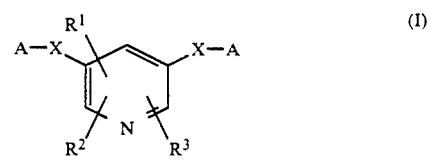

in which
$R^1$, $R^2$, $R^3$, X and A have the abovementioned meaning, has been found, characterized in that ketones of the general formula (VIII)

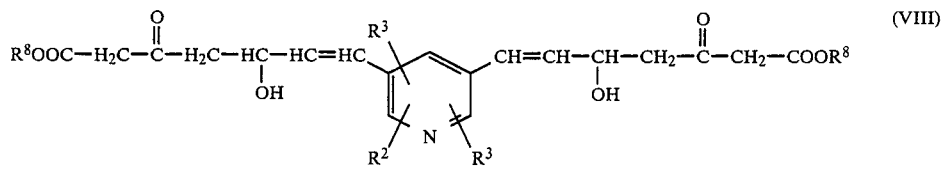

in which

R[1], R[2] and R[3] have the abovementioned meaning, and R[8] - stands for alkyl, are reduced, in the case of the preparation of the acids, the esters are hydrolyzed, in the case of the preparation of the lactones, the carboxylic acids are cyclized, in the case of the preparation of the salts, either the esters or the lactones are hydrolyzed, in the case of the preparation of the ethylene compounds (X=—CH$_2$—CH$_2$—), the ethene compounds (X=—CH=CH—) are hydrogenated according to customary methods, and, if appropriate, isomers are separated.

The process according to the invention can be illustrated by the following formula scheme:

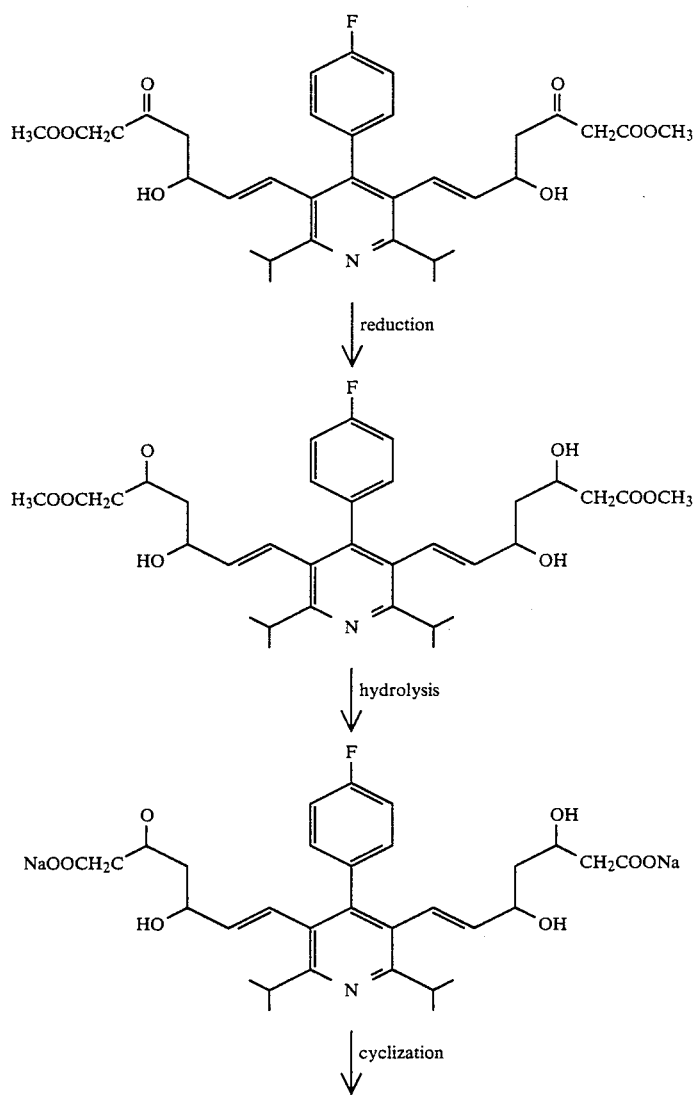

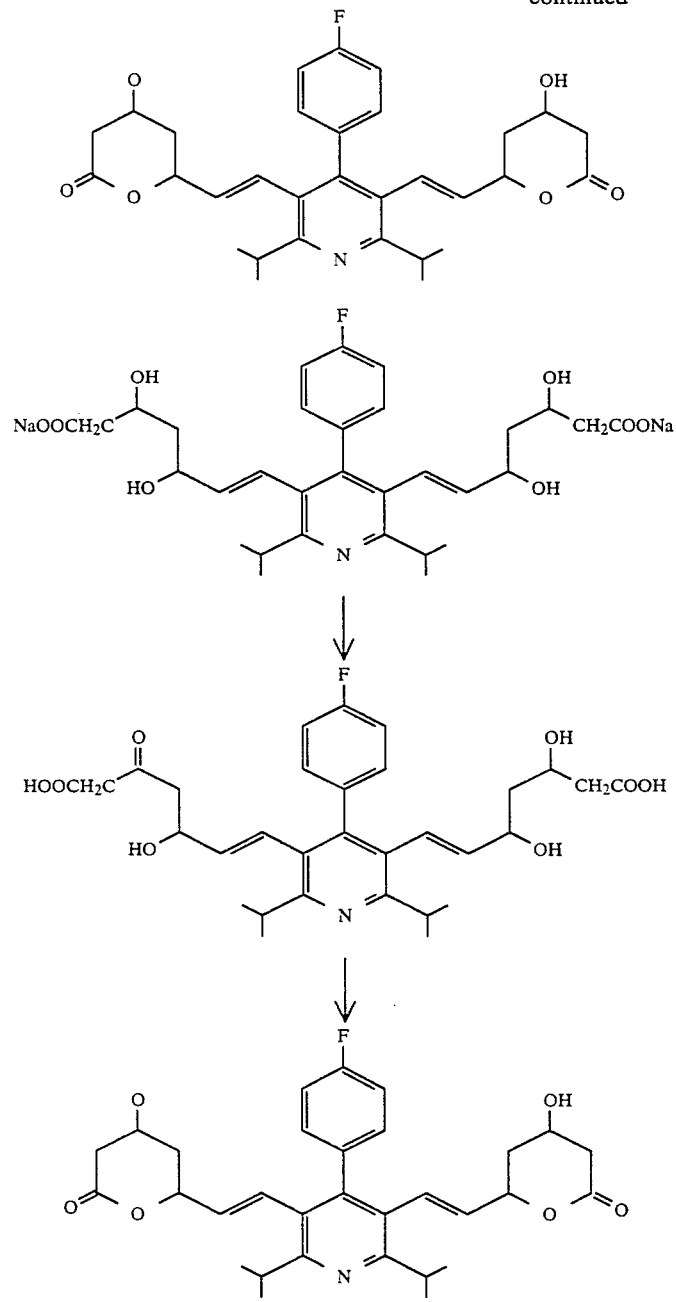

Reduction can be carried out using the customary reductants, preferably using those which are suitable for the reduction of ketones to hydroxyl compounds. In this connection, reduction using metal hydrides or complex metal hydrides in inert solvents, if appropriate in the presence of a trialkylborane, is particularly suitable. Reduction using complex metal hydrides such as, for example, lithium borohydride, sodium borohydride, potassium borohydride, zinc borohydride, lithium trialkyl borohydrides, sodium trialkyl borohydrides, sodium cyanoborohydride or lithium aluminum hydride is preferred. Reduction using sodium borohydride, carried out in the presence of triethylborane, is very particularly preferred.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is likewise possible to employ mixtures of the solvents mentioned.

Reduction of the ketone group to the hydroxyl group is particularly preferably carried out under conditions in which the other functional groups such as, for example, the alkoxycarbonyl group, are not changed. For this, the use of sodium borohydride as a reductant in the presence of triethylborane in inert solvents, such as preferably ether, is particularly suitable.

Reduction in general takes place in a temperature range from −80° C. to +30° C., preferably from −78° C. to 0° C.

Reduction according to the invention is in general carried out at atmospheric pressure. However, it is also possible to carry out the process at underpressure or overpressure (for example in a range from 0.5 to 5 bar).

In general, the reductant is employed in an amount from 1 to 2 moles, preferably from 1 to 1.5 moles, relative to 1 mole of the keto compound.

Under the abovementioned reaction conditions, the carbonyl group is in general reduced to the hydroxyl group, without reduction of the double bond to a single bond taking place.

For the preparation of compounds of the general formula (I), in which X stands for an ethylene grouping, the reduction of the ketones (VIII) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ic)

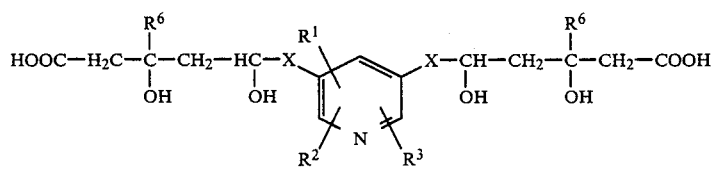

in which
$R^1$, $R^2$, $R^3$, $R^6$ and X have the abovementioned meaning.

The carboxylic acid esters in the context of the general formula (I) correspond to the formula (Id)

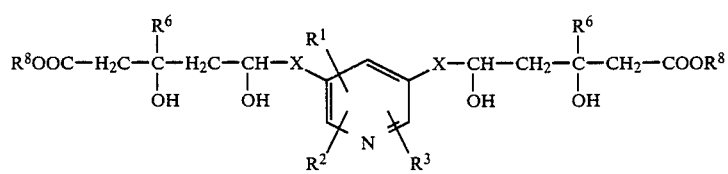

in which
$R^1$, $R^2$, $R^3$, $R^6$ and X have the abovementioned meaning, and
$R^8$ - stands for alkyl.

The salts of the compounds according to the invention in the context of the general formula (I) correspond to the formula (Ie)

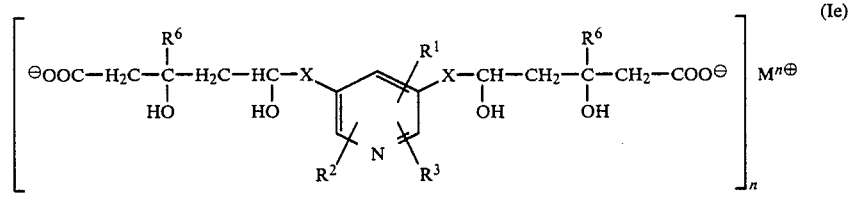

in which
$R^1$, $R^2$, $R^3$, $R^6$ and X have the abovementioned meaning, and
$M^{n\oplus}$ stands for a cation.

The lactones in the context of the general formula (I) correspond to the formula (If)

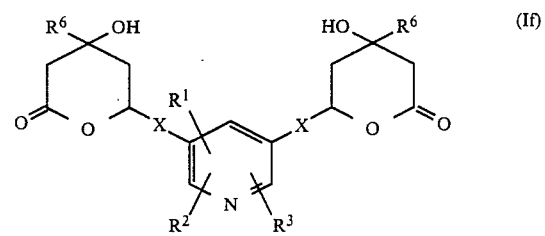

in which
$R^1$, $R^2$, $R^3$, $R^6$ and X have the abovementioned meaning.

For the preparation of the carboxylic acids of the general formula (Ic) according to the invention, the carboxylic acid esters of the general formula (Id) or the lactones of the general formula (If) are in general hydrolyzed by customary methods. Hydrolysis in general takes place by treating the esters or the lactones using customary bases in inert solvents, by means of which the salts of the general formula (Ie) in general first result which can then be converted in a second step into the free acids of the general formula (Ic) by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethylsulphoxide. Alcohols such as methanol, ethanol, propanol or isopropanol are particularly preferably used. It is likewise possible to employ mixtures of the solvents mentioned.

The hydrolysis is in general carried out in a temperature range from 0° C. to +100° C., preferably from 20° C. to +80° C.

In general, the hydrolysis is carried out at atmospheric pressure. However, it is also possible to work at underpressure or overpressure (for example from 0.5 to 5 bar).

When carrying out the hydrolysis, the base is in general employed in an amount from 1 to 3 moles, preferably from 1 to 1.5 moles, relative to 1 mole of the ester or the lactone. Molar amounts of reactants are particularly preferably used.

When carrying out the reaction, the salts of the compounds according to the invention (Ie) are formed in the first step as intermediates which can be isolated. The acids (Ic) according to the invention are obtained by treating the salts (Ie) with customary inorganic acids. These preferably include mineral acids such as, for example, hydrochloric acid, hydrobromic acid, sulphuric acid or phosphoric acid. It has proved advantageous in this connection in the preparation of the carboxylic acids (Ic) to acidify the basic reaction mixture from the hydrolysis in a second step without isolation of the salts. The acids can then be isolated in a customary manner.

For the preparation of the lactones of the formula (If) according to the invention, the carboxylic acids (Ic) according to the invention are cyclized by customary methods, for example by heating the corresponding acid in inert organic solvents, if appropriate in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. It is likewise possible to employ mixtures of the solvents mentioned. Particularly preferably, hydrocarbons, in particular toluene, are used in the presence of molecular sieve.

The cyclization is in general carried out in a temperature range from −40° C. to +200° C., preferably from −25° C. to +50° C.

The cyclization is in general carried out at atmospheric pressure, but it is also possible to carry out the process at underpressure or at overpressure (for example in a range from 0.5 to 5 bar).

Moreover, the cyclization is also carried out in inert organic solvents with the aid of cyclizing or water-eliminating agents. In this connection, carbodiimides are preferably used as water-eliminating agents. Preferably, N,N'-dicyclohexylcarbodiimide paratoluenesulphonate, N-cyclohexyl-N'-[2-(N''-methylmorpholinium)-ethyl]carbodiimide or N-(3-dimethylaminopropyl)-N'-ethyl-carbodiimide hydrochloride are employed as carbodiimides.

Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene, xylene or mineral oil fractions are particularly preferred. Chlorinated hydrocarbons such as, for example, methylene chloride, chloroform or carbon tetrachloride are particularly preferably employed.

The reaction is in general carried out in a temperature range from 0° C. to +80° C., preferably from 10° C. to +50° C.

When carrying out the cyclization, it has proved advantageous to employ the cyclization method with the aid of carbodiimides as dehydrating agents.

The resolution of the isomers into the homogeneous stereoisomeric constituents in general takes place by customary methods, such as are described, for example, by E. L. Eliel, Stereochemistry of Carbon Compounds, McGraw Hill, 1962. In this connection, the resolution of the isomers from the racemic lactone step is preferred. Particularly preferably in this connection, the racemic mixture of the trans-lactones (VII) is converted into the diastereomeric dihydroxyamides (Ig)

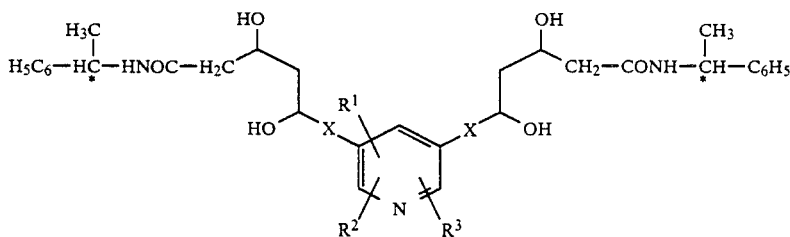

by treating with either D-(+)- or L-(−)-α-methylbenzylamine by customary methods, which can then be resolved into the individual diastereomers by chromatography or crystallization as is customary. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, yields the corresponding pure enantiomeric dihydroxy acids (Ic) which can be converted into the pure enantiomereic lactones by cyclization as described above. In general, it applies that, for the preparation of the compounds of the general formula (I) according to the invention in pure enantiomeric form, the configuration of the final product according to the method described above is dependent on the configuration of the starting materials.

The resolution of isomers is illustrated, for example, in the following scheme:

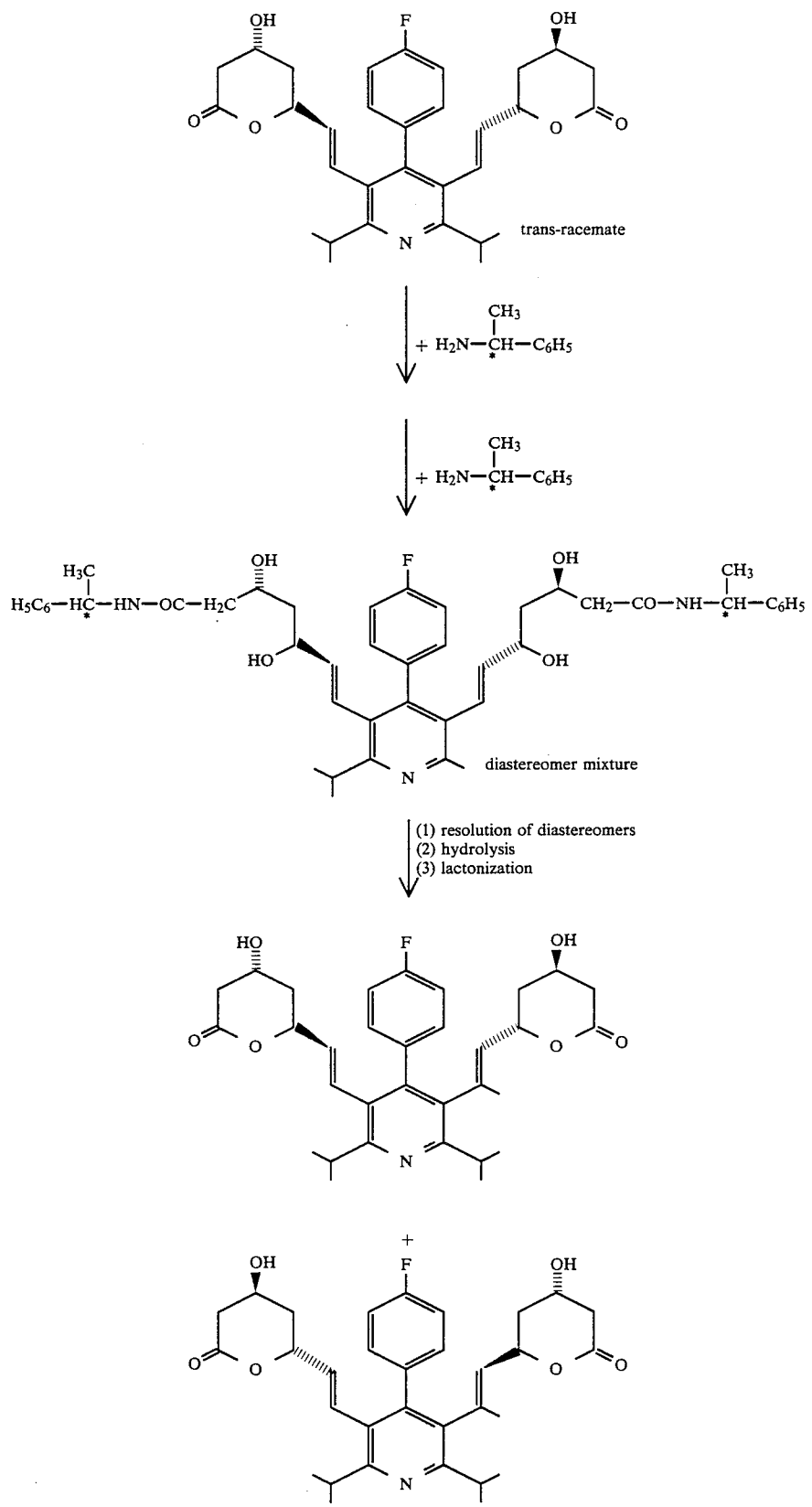
The ketones (VIII) employed as starting materials are new.
A process for the preparation of the ketones of the general formula (VIII) according to the invention

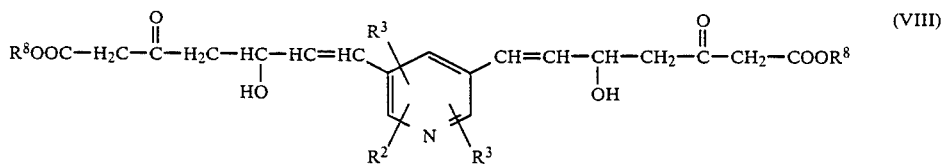

(VIII)

in which
$R^1$, $R^2$ and $R^3$ have the abovementioned meaning and
$R^8$ - stands for alkyl,
has been found, characterized in that aldehydes of the general formula (IX)

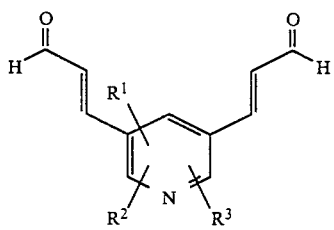

(IX)

in which
$R^1$, $R^2$ and $R^3$ have the abovementioned meaning,
are reacted in inert solvents with acetoacetates of the general formula (X)

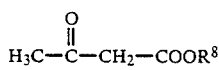

(X)

in which
$R^8$ has the abovementioned meaning, in the presence of bases.

The process according to the invention can, for example, be illustrated by the following scheme:

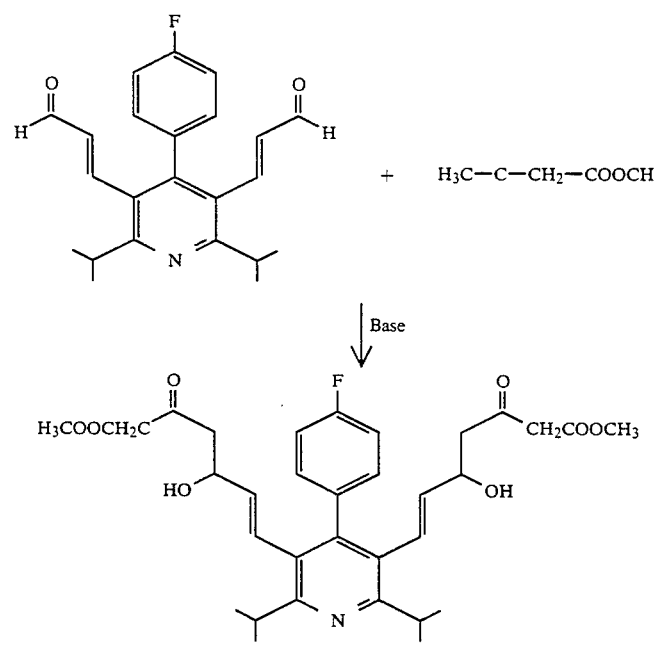

Suitable bases in this connection are the customary strongly basic compounds. These preferably include organolithium compounds such as, for example, N-butyl-lithium, sec.butyllithium, tert.butyllithium or phenyl-lithium, or amides such as, for example, lithium diiso-propylamide, sodium amide or potassium amide, or lithium hexamethyldisilylamide, or alkali metal hydrides such as sodium hydride or potassium hydride. It is likewise possible to employ mixtures of the bases mentioned. N-Butyllithium or sodium hydride or a mixture thereof is particularly preferably employed.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is likewise possible to employ mixtures of the solvents mentioned. Ethers such as diethyl ether or tetrahydrofuran are particularly preferably used.

The reaction is in general carried out in a temperature range from $-80°$ C. to $+50°$ C., preferably from $-20°$ C. to $+30°$ C.

The process is in general carried out at atmospheric pressure, but it is also possible to carry out the process at underpressure or at overpressure, for example in a range from 0.5 to 5 bar.

When carrying out the process, the acetoacetate is in general employed in an amount from 1 to 2, preferably from 1 to 1.5 moles, relative to 1 mole of the aldehyde function.

The acetoacetates of the formula (X) employed as starting materials are known Dr can be prepared by known methods [Beilstein's Handbuch der organischen Chemie (Beilstein's Handbook of Organic Chemistry) III, 632; 438].

Examples of acetoacetates which may be mentioned for the process according to the invention are methyl acetoacetate, ethyl acetoacetate, propyl acetoacetate and isopropyl acetoacetate.

The aldehydes of the general formula (IX) employed as starting materials are new.

The preparation of the aldehydes can be illustrated by the following reaction scheme by way of example for the compounds of the type (Ia):

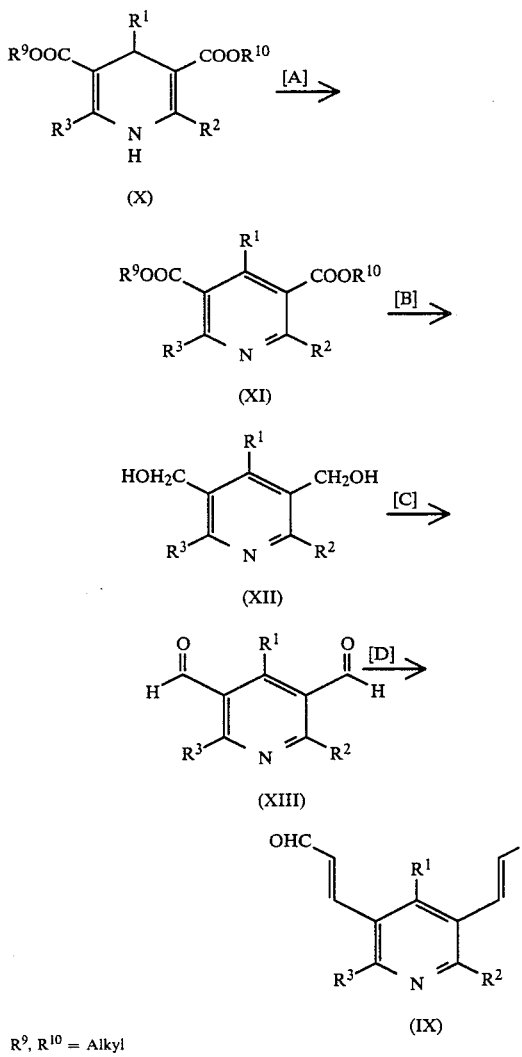

$R^9$, $R^{10}$ = Alkyl

In this connection, the dihydropyridines of the general formula (X) are oxidized in suitable solvents using suitable oxidants in the first step [A]. Preferably, the dihydropyridines are oxidized using 2,2-dichloro-5,6-dicyano-p-benzoquinone at room temperature, or using chromium trioxide in glacial acetic acid at elevated temperatures, preferably under reflux temperature, in chlorinated hydrocarbons such as, for example, methylene chloride to give the pyridines of the formula (XI). In the second step [B], the pyridines (XI) are reduced to the hydroxyl compounds of the general formula (XII) using metal hydrides such as lithium aluminum hydride, sodium cyanoborohydride, diisobutyl aluminum hydride or sodium bis-(2-methoxyethoxy)-dihydroaluminate, in a temperature range from −80° C. to +40° C., preferably from −70° C. to room temperature, in inert solvents such as ethers, for example diethyl ether, dioxane or tetrahydrofuran, preferably in tetrahydrofuran. In the third step [C], the hydroxyl compounds (XII) are oxidized to the aldehydes (XIII) by customary methods using oxidants such as pyridinium chlorochromate, if appropriate in the presence of aluminum oxide, in inert solvents such as chlorinated hydrocarbons, preferably methylene chloride, at room temperature or using trifluoroacetic acid and dimethyl sulphoxide (Swern oxidation) or, however, according to other methods customary for the oxidation of hydroxymethyl compounds to aldehydes. In the fourth step [D], the aldehydes (XIII) are converted into the compounds (IX) by reacting with diethyl-2-(cyclohexylamino)-vinyl phosphonate in inert solvents such as ethers, preferably in tetrahydrofuran in the presence of sodium hydride, in a temperature range from −20° C. to +30° C., preferably from −5° C. to room temperature.

The dihydropyridines of the general formula (X) employed as starting materials are known or can be prepared by known methods [EP-A No. 88,276; DE-A No. 2,847,236].

The compounds of the general formula (I) according to the invention are active compounds for medicaments. In particular, they are inhibitors of 3-hydroxy-3-methylglutaryl coenzyme A (HGM-CoA) reductase and consequently inhibitors of cholesterol biosynthesis. They can therefore be employed for the treatment of hyperlipoproteinaemia, lipoproteinaemia or arteriosclerosis. The active compounds according to the invention in addition cause a lowering of the cholesterol content in the blood.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient to achieve the indicated dosage range.

The formulations are prepared, for example, by extending the active compounds with solvents and/or excipients, if appropriate using emulsifiers and/or dispersing agents, where, for example, in the case of the use of water as a diluent, organic solvents may optionally be used as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, clays, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkyl sulphonates and aryl sulphonates), dispersing agents (for example lignin sulphite waste liquors, methylcellulose, starch and polyvinylpyrrolidone) and lubricants (for example magnesium stearate, talc, stearic acid and sodium lauryl sulphate).

Administration takes place in a customary manner, preferably orally, parenterally, perlingually or intravenously. In the case of oral administration, tablets can, of course, also contain additives, such as sodium citrate, calcium carbonate and dicalcium phosphate together with various additive substances, such as starch, preferably potato starch, gelatin and the like, in addition to the excipients mentioned. Furthermore, lubricants, such as magnesium stearate, sodium lauryl sulphate and talc can also be used for tableting. In the case of aqueous suspensions, various flavor-improvers or colourants can be added to the active compound in addition to the above-mentioned auxiliaries.

In the case of parenteral administration, solutions of the active compounds can be employed using suitable liquid excipients.

In general, it has proved advantageous with intravenous administration to administer amounts of about 0.001 to 1 mg/kg, preferably about 0.01 to 0.5 mg/kg of body weight to obtain effective results, and with oral administration the dosage is about 0.01 to 20 mg/kg, preferably 0.1 to 10 mg/kg of body weight.

Nevertheless, it may be necessary to depart from the amounts mentioned, depending on the body weight or the type of administration route, individual behavior towards the medicament, the manner of its formulation and the point in time or interval at which administration takes place. Thus, in some cases it is sufficient to manage with less than the previously mentioned minimum amount, whereas in other cases the upper limit mentioned must be exceeded. In the case of the administration of larger amounts, it may be advisable to divide these into several individual doses over the day.

PREPARATION EXAMPLES

Example 1

(E/Z)-4-Carboxyethyl-5-(4-fluorophenyl)-2-methyl-pent-4-en-3-one

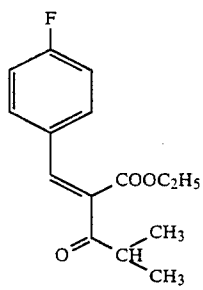

62 g (0.5 mol) of 4-fluorobenzaldehyde and 79 g (0.5 mol) of ethyl isobutanoylacetate are initially introduced into 300 ml of dry isopropanol and a mixture of 2.81 ml (28 mmol) of piperidine and 1.66 ml (29 mmol) of acetic acid in 40 ml of isopropanol is added. The mixture is stirred for 48 h at room temperature and concentrated in vacuo, and the residue is distilled in a high vacuum.

B.p. 0.5 mm : 127° C.

Yield: 108.7 g (82.3% of theory)

Example 2

Diethyl 1,4-dihydro-2,6-diisopropyl-4-(4-fluorophenyl)pyridine-3,5-dicarboxylate

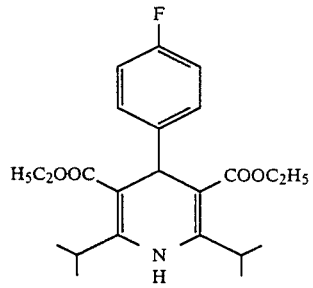

98 g (0.371 mol) of the compound from Example 1 are boiled under reflux for 18 hours with 58.3 g (0.371 mol) of ethyl 3-amino-4-methyl-pent-2-enoate in 300 ml of ethanol. The mixture is cooled to room temperature, the solvent is evaporated off in vacuo and the unreacted starting materials are removed by distillation at 130° C. in a high vacuum. The remaining syrup is stirred with n-hexane and the deposited precipitate is filtered off with suction, washed with n-hexane and dried in a desiccator.

Yield: 35 g (23.4% of theory)

$^1$H-NMR (CDCl$_3$): δ=1.1–1.3 (m, 18H); 4.05–4.25 (m, 6H); 5.0 (s, 1H); 6.13 (s, 1H); 6.88 (m, 2H); 7.2 (m, 2H).

Example 3

Diethyl 2,6-diisopropyl-4-(4-fluorophenyl)-pyridine-3,5-dicarboxylate

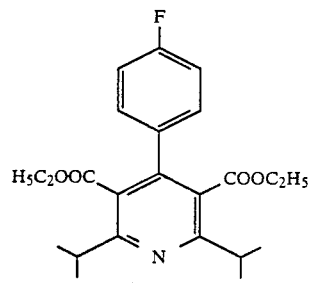

3.8 g (16.4 mmol) of 2,3-dichloro-5,6-dicyano-p-benzoquinone are added to a solution of 6.6 g (16.4 mmol) of the compound from Example 2 in 200 ml of methylene chloride p.a. and the mixture is stirred for 1 h at room temperature. It is then filtered over kieselgur with suction, the methylene chloride phase is extracted three times using 100 ml of water each time and dried over magnesium sulphate. After concentrating in vacuo, the residue is chromatographed on a column (100 g of silica gel 70–230 mesh, φ 3.5 cm, using ethyl acetate/petroleum ether (1:9).

Yield 5.8 g (87.9% of theory)

$^1$H-NMR (CDCl$_3$): δ=0.98 (t, 6H); 1.41 (d, 12H); 3.1 (m, 2H); 4.11 (q, 4H); 7.04 (m, 2H); 7.25 (m, 2H).

Example 4

3,5-Dihydroxymethyl-2,6-diisopropyl-4-(4-fluorophenyl)-pyridine

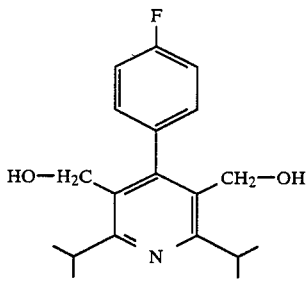

22.8 ml (80 mmol) of a 3.5 molar solution of sodium bis-(2-methoxyethoxy)-dihydroaluminate in toluene are added under nitrogen to a solution of 4.6 g (11.4 mmol) of the compound from Example 3 in 100 ml of dry tetrahydrofuran at −10° C. to −5° C. The mixture is stirred overnight at room temperature and then warmed to 40° C. for 5 h. After cooling again to 0° C., 100 ml of water are cautiously added dropwise and the mixture is extracted three times using 100 ml of ethyl acetate each time. The combined organic phases are washed with saturated sodium chloride solution, dried over magnesium sulphate and concentrated in vacuo. The residue is chromatographed on a column (100 g of silica gel 70–230 mesh, φ 3.5 cm, using ethyl acetate/petroleum ether (6:4)).

Yield: 2.4 g (66.7% of theory)

$^1$H-NMR (CDCl$_3$): δ=1.35 (d, 12H); 3.43 (m, 2H); 4.47 (d, 4H); 7.05–7.3 (m, 4H).

Example 5

2,6-Diisopropyl-4-(4-fluorophenyl)-pyridine-3,5-dicarbaldehyde

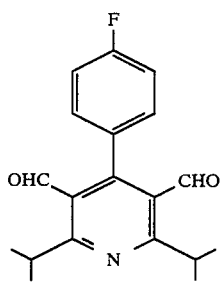

10.3 g (48 mmol) of pyridinium chlorochromate and 4.9 g (48 mmol) of neutral alumina are added to a solution of 3.8 g (12 mmol) of the compound from Example 4 in 100 ml of methylene chloride p.a. and the mixture is stirred for 1 h at room temperature. The mixture is filtered over kieselgur with suction and washed with 300 ml of methylene chloride. The methylene chloride phase is concentrated in vacuo and the residue is chromatographed on a column (150 g of silica gel 70–230 mesh, φ3.5 cm, using ethyl acetate/petroleum ether 2:8).

Yield: 3.2 g (85.3% of theory)

$^1$H-NMR (CDCl$_3$): δ=1.33 (d, 12H); 3.85 (m, 2H); 7.1–7.32 (m, 4H); 9.8 (s, 2H).

Example 6

(E,E)-2,6-Diisopropyl-4-(4-fluorophenyl)-3,5-di(prop-2-en-1-al-3-yl)-pyridine

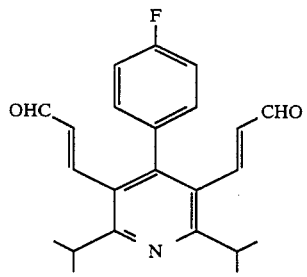

3.1 g (12 mmol) of diethyl 2-(cyclohexylamino)vinyl phosphonate dissolved in 20 ml of dry tetrahydrofuran are added dropwise under nitrogen to a suspension of 0.36 g (12 mmol) of 80% pure sodium hydride in 20 ml of dry tetrahydrofuran at −5° C. After 30 minutes, 1.6 g (5 mmol) of the compound from Example 5 in 20 ml of dry tetrahydrofuran are added dropwise at the same temperature and the mixture is warmed to reflux for 30 minutes. After cooling to room temperature, the batch is added to 200 ml of ice-cold water and extracted three times using 100 ml of ethyl acetate each time. The combined organic phases are washed with saturated sodium chloride solution and dried over magnesium sulphate. After concentrating in vacuo, the residue is taken up in 50 ml of toluene, a solution of 2 g (15 mmol) of oxalic acid dihydrate in 25 ml of water is added and the mixture is warmed to reflux for 30 minutes. After cooling to room temperature, the phases are separated, and the organic phase is washed with saturated sodium chloride solution, dried over magnesium sulphate and concentrated in vacuo. The residue is chromatographed on a column (100 g of silica gel 70–230 mesh, φ3.5 cm, using ethyl acetate/petroleum ether 2:8).

Yield: 920 mg (50% of theory)

$^1$H-NMR (CDCl$_3$): δ=1.33 (d, 12H); 3.33 (m, 2H); 6.03 (dd, 2H); 7.0–7.35 (m, 6H); 9.42 (d, 2H).

Example 7

2,6-Diisopropyl-4-(4-fluorophenyl)-3,5-di-(methyl (E)-5-hydroxy-3-oxo-hept-6-enoat-7-yl)-pyridine

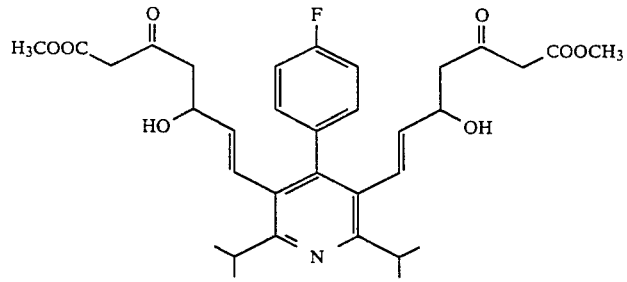

1.16 g (10 mmol) of methyl acetate in 5 ml of dry tetrahydrofuran are added dropwise under nitrogen to a suspension of 360 mg (12 mmol) of 80% pure sodium hydride in 30 ml of dry tetrahydrofuran at −5° C. After 15 minutes, 6.2 ml (10 mmol) of 15% strength butyllithium in n-hexane are added dropwise at the same temperature and the mixture is stirred for 15 minutes, 912 mg (2.5 mmol) of the compound from Example 6 dissolved in 20 ml of dry tetrahydrofuran are subsequently added dropwise and the mixture is stirred at −5° C. for 30 minutes. 3 ml of 50% strength acetic acid are cautiously added to the reaction solution, and the mixture is diluted using 100 ml of water and extracted three times using 100 ml of ether each time. The combined organic phases are washed twice with saturated sodium hydrogen carbonate solution and once with saturated sodium chloride solution, dried over magnesium sulphate and concentrated in vacuo. The residue is chromatographed on a column (80 g of silica gel 70–230 mesh, 3 cm, using ethyl acetate/petroleum ether 1:1).

Yield: 800 mg (53.6% of theory)

$^1$H-NMR (CDCl$_3$): δ=1.25 (m, 12H); 2.47 (m, 4H); 3.25 (m, 2H); 3.42 (s, 4H); 3.73 (s, 6H); 4.5 (m, 2H); 5.25 (dd, 2H); 6.35 (dd, 2H); 7.0 (m, 4H).

Example 8

2,6-Diisopropyl-4-(4-fluorophenyl)-3,5-di-(methyl erythro-(E)-3,5-dihydroxy-hept-6-enoat-7-yl)-pyridine

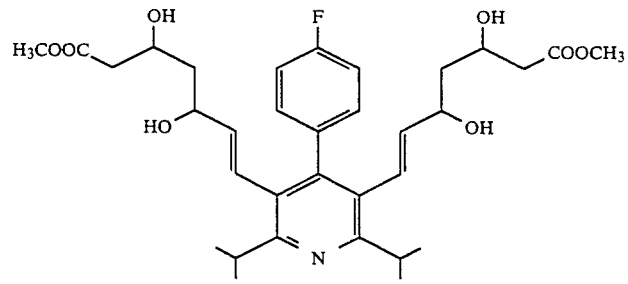

3.2 ml (3.2 mmol) of 1M triethylborane solution in tetrahydrofuran are added at room temperature to a solution of 776 mg (1.3 mmol) of the compound from Example 7 in 30 ml of dry tetrahydrofuran, air is passed through the solution for 5 minutes and it is cooled to −30° C. internal temperature. 122 mg (3.2 mmol) of sodium borohydride are added and, slowly, 2.5 ml of methanol, the mixture is stirred for 30 minutes at −30° C. and then a mixture of 10 ml of 30% strength hydrogen peroxide and 20 ml of water is added. The temperature is allowed to climb to 0° C. in the course of this and the mixture is stirred for a further 30 minutes. The mixture is extracted three times using 50 ml of ethyl acetate each time, and the combined organic phases are washed once each with saturated sodium hydrogen carbonate solution and saturated sodium chloride solution, dried over magnesium sulphate and concentrated in vacuo. The residue is chromatographed on a column (50 g of silica gel 230–400 mesh, φ2.5 cm, using ethyl acetate/petroleum ether 1:1).

Yield: 400 mg (51.4% of theory) hu H-NMR (CDCl$_3$): δ=12.5 (m, 12H); 1.4 (m, 4H); 2.42 (m, 4H); 3.3 (m, 2H); 3.72 (s, 6H); 4.1 (m, 2H); 4.3 (m, 2H); 5.25 (dd, 2H); 6.3 (dd, 2H); 7.0 (m, 4H).

Example 9

(E/Z)-4-Carboxyethyl-2-methyl-5-phenyl-pent-4-en-3-one

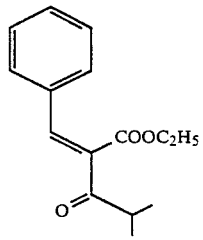

6.9 g (0.44 mol) of ethyl isobutanoylacetate and 6.3 g (0.44 mol) of benzaldehyde are initially introduced into 300 ml of isopropanol, a mixture of 2.5 ml (25 mmol) of piperidine and 1.5 ml (26 mmol) of acetic acid in 40 ml of isopropanol is added and the mixture is stirred for 24 h at room temperature. The mixture is concentrated in vacuo and the residue is distilled in a high vacuum.

B.p. 0.5 mm : 130° C.

Yield: 60.7 g (56.2% of theory)

Example 10

Diethyl 1,4-dihydro-2,6-diisopropyl-4-phenyl-pyridine-3,5-dicarboxylate

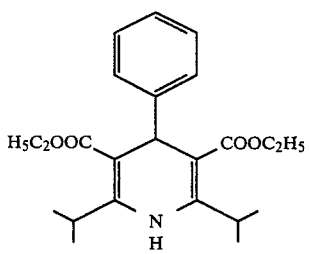

29.5 g (120 mmol) of the compound from Example 9 and 18.8 g (120 mmol) of ethyl 3-amino-4-methyl-pent-2-en-oate are boiled under reflux in 150 ml of ethanol for 8 hours. The mixture is cooled and concentrated in vacuo, and the residue is chromatographed on a column (500 g of silica gel, 70–230 mesh, $\phi$ 5 cm, using ethyl acetate/petroleum ether 1:9).

Yield: 7.2 g (15.1% of theory)

$^1$H-NMR (CDCl$_3$): $\delta$=1.2 (m, 18 H); 4.1 (m, 4H); 4.21 (m, 2H); 5.02 (s, 1H); 6.13 (s, 1H); 7.2 (m, 5H).

Example 11

Diethyl 2,6-diisopropyl-4-phenyl-pyridine-3,5dicarboxylate

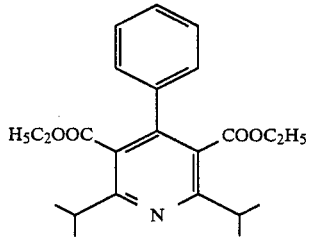

7.2 g (18.2 mmol) of the compound from Example 10 are reacted analogously to Example 3. Yield: 6.4 g (88.8% of theory)

Example 12

3,5-Dihydroxymethyl-2,6-diisopropyl-4-phenyl-pyridine

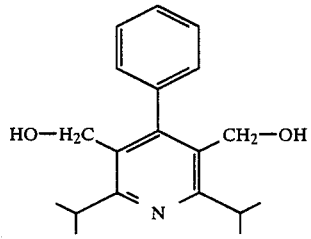

40.5 ml (40.5 mmol) of a 1 molar solution of lithium aluminum hydride in ether are added dropwise under nitrogen to a solution of 6.4 g (16.2 mmol) of the compound from Example 11 in 100 ml of dry tetrahydrofuran at 0° C. The mixture is stirred overnight at room temperature, warmed to 50° C. for 3 h and cooled again to 0° C. 200 ml of water are cautiously added dropwise to the mixture, and it is filtered over kieselguhr with suction and washed with 250 ml of ether. The organic phase is separated, washed once with saturated sodium chloride solution, dried over magnesium sulphate and concentrated in vacuo. The residue is stirred with petroleum ether, and the precipitate is filtered off with suction and dried in a desiccator.

Yield: 4 g (83.3% of theory)

$^1$H-NMR (CDCl$_3$): $\delta$=1.3 (d, 12H); 3.5 (m, 2H); 4.3 (d, 4H); 7.35 (m, 5H).

Example 13

2,6-Diiopropyl-4-phenyl-pyridine-3,5-dicarbaldehyde

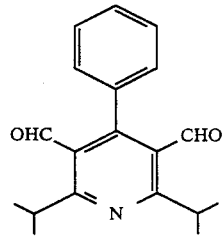

4 g (13.3 mmol) of the compound from Example 12 are reacted analogously to Example 5. Yield: 3.4 g (87.2% of theory)

$^1$H-NMR (CDCl$_3$): $\delta$=1.35 (d, 12H); 3.4 (m, 2H); 7.3 (m, 2H); 7.5 (m, 3H); 9.3 (s, 2H).

Example 14

(E,E)-2,6-Diisopropyl-4-phenyl-3,5-di-(prop-2-en-1-al-3-yl)-pyridine

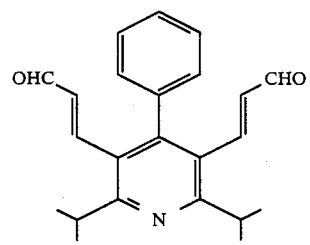

3.35 g (11.4 mmol) of the compound from Example are reacted analogously to Example 6. Yield: 2.7 g (67.5% of theory)

$^1$H-NMR (CDCl$_3$): $\delta$=1.35 (d, 12H); 3.47 (m, 2H); 6.04 (dd, 2H); 7.0–7.45 (m, 7H); 9.4 (d, 2H).

Example 15

2,6-Diisopropyl-4-phenyl-3,5-di-(methyl (E)-5-hydroxy-3-oxo-hept-6-enoat-7-yl)-pyridine

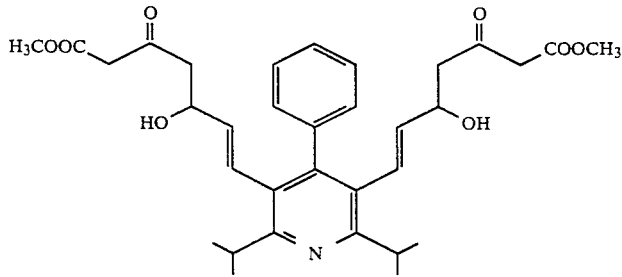

2.7 g (7.8 mmol) of the compound from Example 14 are reacted analogously to Example 7. Yield: 3.2 g (71.1% of theory)

$^1$H-NMR (CDCl$_3$): δ=1.25 (m, 12H); 2.35 (m, 4H); 3.27 (m, 2H); 3.40 (s, 4H); 3.75 (s, 6H); 4.38 (m, 2H); 5.25 (dd, 2H); 6.37 (dd, 2H); 7.02 (m, 2H); 7.30 (m, 3H).

Example 16

2,6-Diisopropyl-4-phenyl-3,5-di-(methyl erythro-(E)-3,5-dihydroxy-hept-6-enoat-7-yl)-pyridine

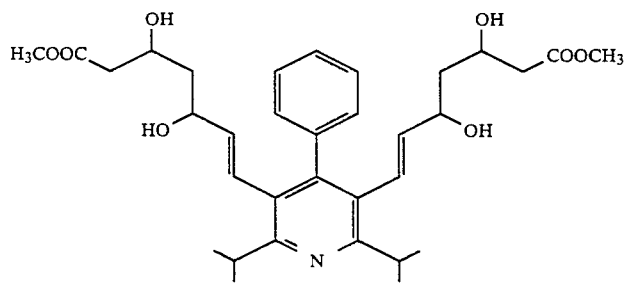

3.2 g (5.5 mmol) of the compound from Example 15 are reacted analogously to Example 8. Yield: 2 g (62.5% of theory)

$^1$H-NMR (CDCl$_3$): δ=1.25 (m, 12H); 1.3–1.7 (m, 4H); 2.39 (m, 4H); 3.2–3.4 (m, 2H); 3.71 (s, 6H); 4.02 (m, 2H); 4.27 (m, 2H); 5.3 (m, 2H); 6.32 (m, 2H); 7.0 (m, 2h); 7.25 (m, 3H).

Example 17

(E/Z)-2-Ethoxycarbonyl-1-(4-fluorophenyl)-but-2-en-3-one

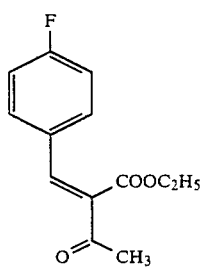

62 g (0.5 mol) of 4-fluorobenzaldehyde and 53.9 ml (0.5 mol) of methyl acetoacetate are initially introduced into 30 ml of isopropanol, a mixture of 2.81 ml (28 mmol) of piperidine and 1.66 ml (29 mmol) of acetic acid in 40 ml of isopropanol is added and the mixture is stirred for 48 h at room temperature. The mixture is concentrated in vacuo and the residue is distilled in a high vacuum.

B.p. 0.5 mm: 138° C.

Yield: 50.5 g (45.5% of theory)

Example 18

Dimethyl 1,4-dihydro-2,6-dimethyl-4-(4-fluorophenyl)-pyridine-3,5-dicarboxylate 33.3 g (0.15 mol) of the compound from Example 17 are boiled under reflux for 4 h with 17.3 g (0.15 mol) of methyl 3-aminocrotonate in 150 ml of ethanol. The mixture is cooled to 0° C., and the deposited precipitate is filtered off with suction, washed with a little petroleum ether and dried in a desiccator.

Yield: 32 g (66.8% of theory)

$^1$H-NMR (CDCl$_3$): δ=2.33 (s, 6H); 3.65 (s, 6H); 4.99 (s, 1H); 5.77 (s, 1H); 6.89 (m, 2H); 7.22 (m, 2H).

Example 19

Dimethyl 2,6-dimethyl-4-(4-fluorophenyl)-pyridine-3,5-dicarboxylate

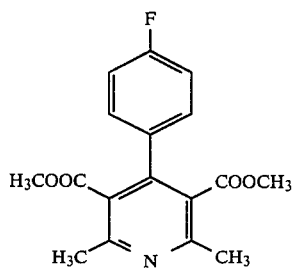

32 g (0.1 mol) of the compound from Example 18 are reacted analogously to Example 3.

Yield: 27.2 g (87% of theory)

$^1$H-NMR (CDCl$_3$): δ=2.59 (s, 6H); 3.56 (s, 6H); 7.08 (m, 2H); 7.25 (m, 2H).

Example 20

3,5-Dihydroxymethyl-2,6-dimethyl-4-(4-fluorophenyl)-pyridine

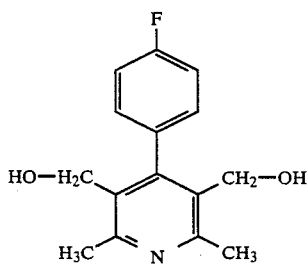

25 ml (87.5 mmol) of a 3.5 molar solution of sodium bis-(2-methoxyethoxy)-dihydroaluminate in toluene are added under nitrogen to a solution of 7.9 g (25 mmol) of the compound from Example 19 in 100 ml of dry tetrahydrofuran at 0° C. The mixture is stirred at room temperature for 6 h, cooled again to 0° C. and 200 ml of water are slowly added dropwise. The mixture is extracted three times using 150 ml of ethyl acetate each time, the combined organic phases are washed once with saturated sodium chloride solution, dried over magnesium sulphate and concentrated in vacuo. The residue is stirred with ether, filtered off with suction and dried in a desiccator.

Yield: 3.5 g (53.8% of theory)

$^1$H-NMR (CDCl$_3$): δ=2.81 (s, 6H); 4.28 (d, 4H); 7.1 (m, 2H); 7.3 (m, 2H).

Example 21

2,6-Dimethyl-4-(4-fluorophenyl)-pyridine-3,5-carbaldehyde

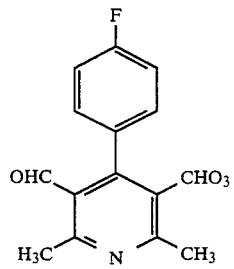

3.5 g (13.4 mmol) of the compound from Example 20 are reacted analogously to Example 5.

Yield: 1.7 g (53% of theory)

$^1$H-NMR (CDCl$_3$): δ=2.88 (s, 6H); 7.28 (m, 4H); 9.82 (s, 2H).

Example 22

(E,E)-2,6-Dimethyl-4-(4-fluorophenyl)-3,5-bis-(propen-1-al-3-yl)-pyridine

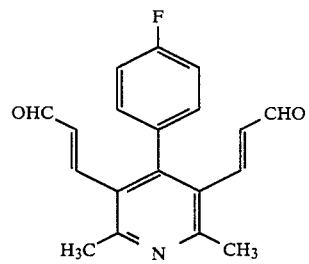

1.7 g (7 mmol) of the compound from Example 21 are reacted analogously to Example 6.

Yield: 1 g (47.6% of theory)

$^1$H-NMR (CDCl$_3$): δ=2.7 (s, 6H); 6.15 (dd, 2H); 7.15 (m, 6H); 9.43 (d, 2H).

Example 23

2,6-Dimethyl-4-(4-fluorophenyl)-3,5-di-(methyl (E)-5-hydroxy-3-oxo-hept-6-enoat-7-yl)-pyridine

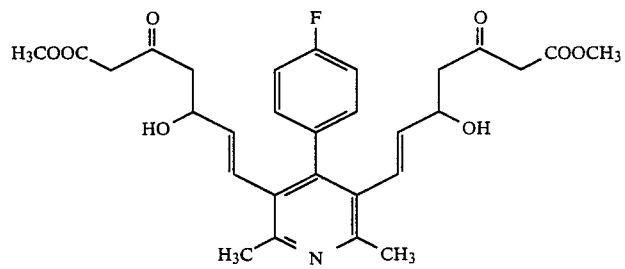

1 g (3.2 mmol) of the compound from Example 22 are reacted analogously to Example 7.

Yield: 1 g (57% of theory)

$^1$H-NMR (CDCl$_3$): δ=2.50 (m, 4H); 2.55 (s, 6H); 3.45 (s, 4H); 3.73 (s, 6H); 4.52 (m, 2H); 5.35 (dd, 2H); 6.28 (d, 2H); 7.05 (m, 4H) ppm.

Example 24

2,6-Dimethyl-4-(4-fluorophenyl)-3,5-di-(methyl erythro-(E)-3,5-dihydroxy-hept-6-enoat-7-yl)-pyridine

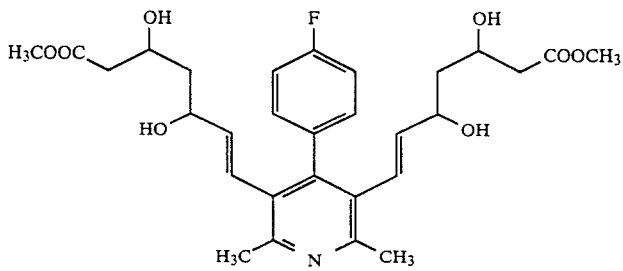

1 g (1.8 mmol) of the compound from Example 23 are reacted analogously to Example 8.
Yield: 0.7 g (69.9% of theory)
$^1$H-NMR (CDCl$_3$): δ=1.20–1.60 (m, 4H); 2.43 (m, 4H); 2.54 (s, 6H); 3.72 (s, 6H); 4.09 (m, 2H); 4.33 (m, 2H); 5.37 (dd, 2H); 6.22 (d, 2H); 7.03 (m, 4H) ppm.

Example 25

5-Ethyl 5-methyl 1,4-dihydro-4-(4-fluorophenyl)-2-isopropyl-6-methyl-pyridine-3,5-dicarboxylate

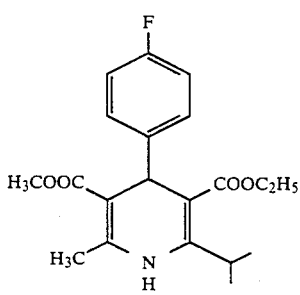

15 g (56.8 mol) of the compound from Example 1 and 6.5 g (56.8 mmol) of methyl 3-aminocrotonate are boiled to reflux in 150 ml of ethanol for 20 h. The mixture is cooled, filtered and concentrated in vacuo. The residue is chromatographed on a column (250 g of silica gel 70–230 mesh, φ 4.5 cm, using ethyl acetate/petroleum ether 3:7).
Yield: 13.6 g (66.3% of theory)
$^1$H-NMR (CDCl$_3$): δ=1.2 (m, 9H); 2.35 (s, 3H); 3.65 (s, 3H); 4.12 (m, 3H); 4.98 (s, 1H); 5.75 (s, 1H); 6.88 (m, 2H); 7.25 (m, 2H).

Example 26

3-Ethyl 5-methyl 4-(4-fluorophenyl)-2-isopropyl-6-methylpyridine-3,5-dicarboxylate

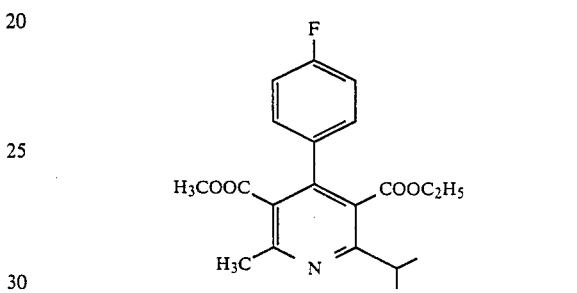

13.5 g (37.4 mmol) of the compound from Example 25 are reacted analogously to Example 3.
Yield: 9.5 g (79.9% of theory)
$^1$H-NMR (CDCl$_3$): δ=0.98 (t, 3H); 1.31 (d, 6H); 2.6 (s, 3H); 3.11 (m, 1H); 3.56 (s, 3H); 4.03 (q, 2H); 7.07 (m, 2H); 7.25 (m, 2H).

Example 27

3,5-Dihydroxymethyl-4-(4-fluorophenyl)-2-isopropyl-6-methyl-pyridine

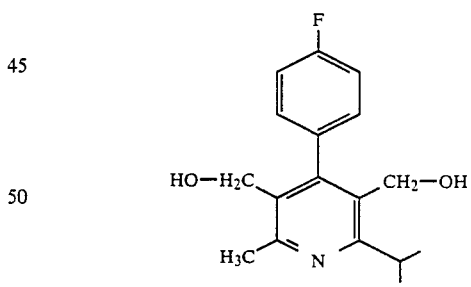

20.7 g (57.7 mmol) of the compound from Example 26 dissolved in 50 ml of absolute tetrahydrofuran are slowly added dropwise under nitrogen to a suspension of 6 g (158 mmol) of lithium aluminum hydride in 200 ml of absolute tetrahydrofuran at 60° C. The mixture is heated to reflux for 1 h, cooled to 0° C. and 18 ml of water are cautiously added. 6 ml of 10% strength potassium hydroxide solution are added to the mixture, it is filtered off from the precipitate with suction and the residue is boiled twice using 250 ml of ether each time. The combined mother liquors are dried over magnesium sulphate and concentrated in vacuo. The residue is stirred with petroleum ether, filtered off with suction and dried in a desiccator.

Yield: 11.5 g (68.9% of theory)
1H-NMR (CDCl3): δ=1.3 (d, 6H); 2.69 (s, 3H); 3.51 (m, 1H); 4.3 (m, 4H); 7.1 (m, 2H); 7.3 (m, 2H).

Example 28

4-(4-Fluorophenyl)-2-isopropyl-6-methyl-pyridine-3,5-dicarbaldehyde dicarbaldehyde

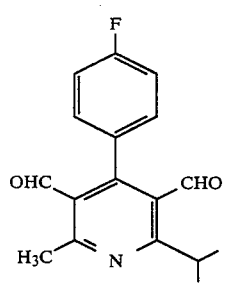

11.5 g (40 mmol) of the compound from Example 27 are reacted analogously to Example 5.
Yield: 7.3 g (64% of theory)
1H-NMR (CDCl3): δ=1.32 (d, 6H); 2.88 (s, 3H); 3.87 (m, 1H); 7.25 (m, 4H); 9.81 (d, 2H).

Example 29

(E,E)-4-(4-Fluorophenyl)-2-isopropyl-6-methyl-3,5-di-(prop-2-en-1-al-3-yl)-pyridine

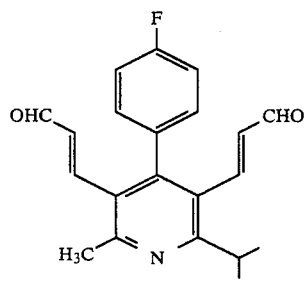

7.3 g (21.7 mmol) of the compound from Example are reacted analogously to Example 6.
Yield: 6.35 g (86.9% of theory)
1H-NMR (CDCl3): δ=1.32 (d, 6H); 2.7 (s, 3H); 3.34 (m, 1H); 6.02 (dd, 1H); 6.15 (dd, 1H); 7.0–7.35 (m, 6H); 9.42 (d, 1H); 9.43 (d, 1H).

Example 30

4-(4-Fluorophenyl)-2-isopropyl-6-methyl-3,5-di-(methyl (E)-5-hydroxy-3-oxo-hept-6-enoat-7-yl)-pyridine

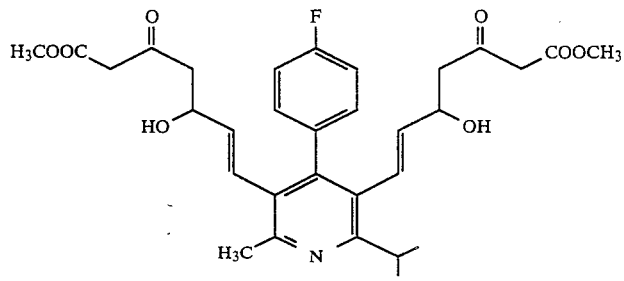

6.3 g (18.8 mol) of the compound from Example 29 are reacted analogously to Example 7.
Yield: 5.7 g (53.5% of theory)
1H-NMR (CDCl3): δ=1.25 (d, 6H); 2.42 (m, 2H); 2.53 (m, 2H); 2.57 (s, 3H); 3.28 (m, 1H); 3.42 (s, 2H); 3.43 (s, 2H); 3.75 (s, 6H); 4.52 (m, 2H); 5.25.(dd, 1H); 5.36 (dd, 1H); 6.28 (d, 1H); 6.37 (d, 1H); 6.90–7.20 (m, 4H).

Example 31

4-(4-Fluorophenyl)-2-isopropyl-6-methyl-3,5-di-(methyl erythro-(E)-3,5-dihydroxy-hept-6-enoat-7-yl)-pyridine

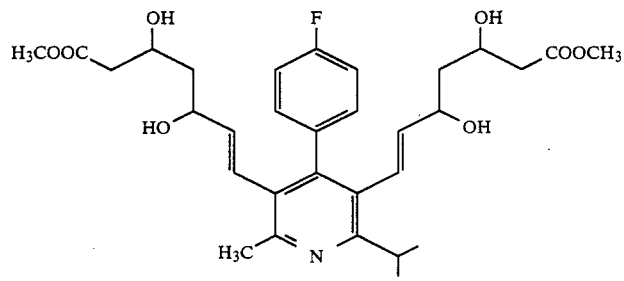

5.7 g (10 mmol) of the compound from Example 30 are reacted analogously to Example 8.
Yield: 2.9 g (50.8% of theory)
1 1H-NMR (CDCl3): δ=1.25 (m, 6H); 1.2 - 1.5 (m, 4H); 2.41 (m, 4H); 2.57 (s, 3H); 3.3 (m, 1H); 3.72 (s, 6H);4.1 (m, 2H); 4.3 (m, 2H); 5.15–5.5 (m, 2H); 6.15–6.45 (m, 2H); 7.0 (m, 4H).

Example 32

Diethyl 1,4-dihydro-2-ethyl-4-(4-fluorophenyl)-6-isopropyl-pyridine-3,5-dicarboxylate

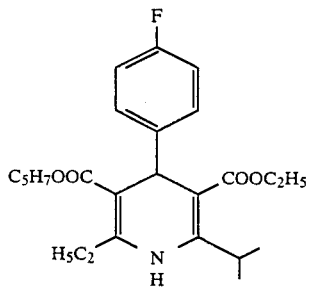

9.5 g (73.6 mmol) of ethyl 3-amino-pent-2-enoate and 19.4 g (73.6 mmol) of the compound from Example are boiled under reflux for 5 hours in 200 ml of n-butanol. The mixture is cooled to room temperature, the solvent is concentrated in vacuo and the residue is chromatographed on a column (silica gel 70–230 mesh, using petroleum ether/ethyl acetate 9:1).
Yield: 5.3 g (19.3% of theory)

Example 33

2-Ethyl-4-(4-fluorophenyl)-6-isopropyl-3,5-di-(methyl erythro-(E)-3,5-dihydroxy-hept-6-enoat-7-yl)-pyridine

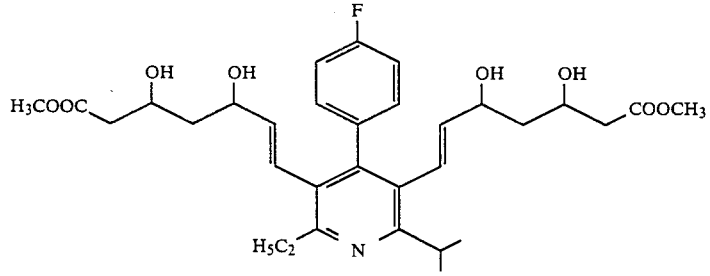

Example 33 was prepared from the compound from Example 32, in analogy to the reactions of Examples 3, 27, 5, 6, 7 and 8:

$^1$H-NMR (CDCl$_3$): δ=1.28 (m, 9H); 1.43 (m, 4H); 2.42 (m, 4H); 2.82 (q, 2H); 3.32 (m, 1H); 3.72 (s, 6H); 4.09 (m, 2H); 4.32 (m, 2H); 5.28 (m, 2H); 6.30 (m, 2H); 7.00 (m, 4H) ppm

Example 34

Diethyl 1,4-dihydro-4-(4-fluorophenyl)-2-isopropyl-6-n-propyl-pyridine-3,5-dicarboxylate

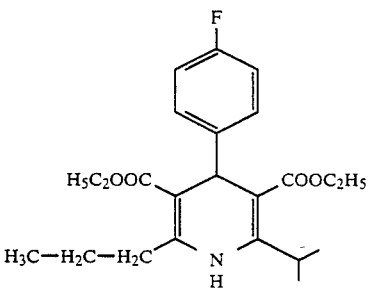

5.8 g (36.8 mmol) of ethyl 3-amino-hex-2-enoate and 9.7 g (36.8 mmol) of the compound from Example 1 are boiled under reflux for 48 hours in 100 ml of ethanol p.A. The mixture is cooled, the solvent is concentrated in vacuo and the residue is chromatographed on a column (silica gel 70–230 mesh, using petroleum ether/ethyl acetate 8:2).
Yield: 2.6 g (17.7% of theory).

Example 35

4-(4-Fluorophenyl)-2-isopropyl-6-n-propyl-3,5-di-(methyl erythro-(E)-3,5-dihydroxy-hept-6-enoat-7-yl)-pyridine

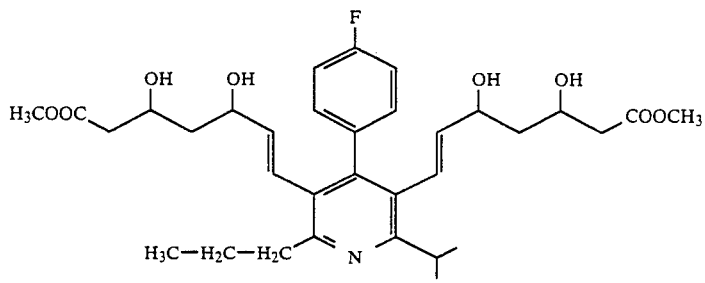

Example 35 was prepared from the compound from Example 34, in analogy to the reactions of Examples 3, 27, 5, 6, 7 and 8.

$^1$H-NMR (CDCl$_3$): δ=0.98(t, 3H); 1.22 (d, 6H); 1.38 (m, 4H); 1.77 (m, 2H); 2.40 (m, 4H); 2.78 (m, 2H); 3.28 (m, 1H); 3.70 (s, 6H); 4.05 (m, 2H); 4.28 (m, 2H); 5.25 (m, 2H); 6.28 (m, 2H); 6.95 (m, 4H) ppm.

Example 36

Diethyl
1,4-dihydro-2-n-butyl-4-(4-fluorophenyl)-6-isopropyl-pyridine-3,5-dicarboxylate

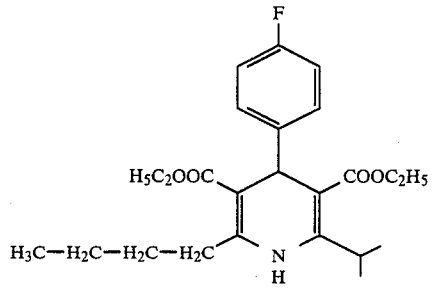

6.3 g (36.8 mmol) of ethyl 3-amino-hept-2-enoate and 9.7 g (36.8 mmol) of the compound from Example 1 are reacted analogously to Example 34.
Yield: 2.5 g (16.4% of theory)

Example 37

2-n-Butyl-4-(4-fluorophenyl)-6-isopropyl-3,5-di-(methyl erythro-(E)-3,5-dihydroxy-hept-6-enoat-7-yl)-pyridine

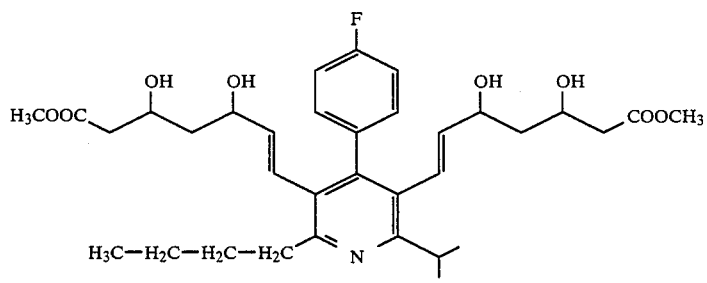

Example 37 was prepared from the compound from Example 36, in analogy to the reactions of Examples 3, 27, 5, 6, 7 and 8.

Example 38

Diethyl
1,4-dihydro-2-benzyl-4-(4-fluorophenyl)-6-isopropyl-pyridine-3,5-dicarboxylate

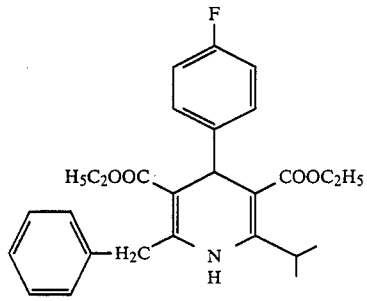

7.4 g (36.8 mmol) of ethyl 3-amino-4-phenylcrotonate and 9.7 g (36.8 mmol) of the compound from Example 1 are reacted analogously to Example 34.
Yield: 2.1 g (12.6% of theory).

Example 39

2-Benzyl-4-(4-fluorophenyl)-6-isopropyl-3,5-di-(methylerythro-(E)-3,5-dihydroxy-hept-6-enoat-7-yl)-pyridine

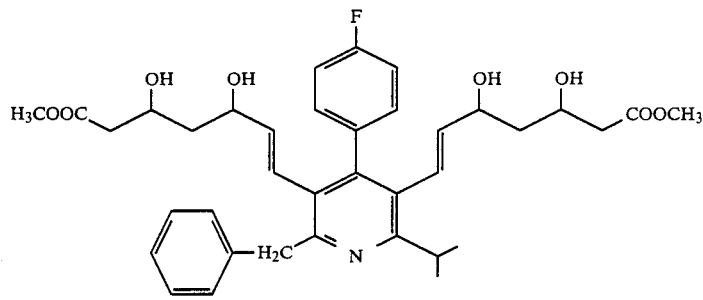

Example 39 was prepared from the compound from Example 38, in analogy to the reactions of Examples 3, 27, 5, 6, 7 and 8.

$^1$H-NMR (CDCl$_3$): δ=1.10–1.50 (m, 10H); 2.40 (m, 4H); 3.32 (m, 1H); 3.72 (s, 3H); 3.73 (s, 3H); 3.98 (m, 1H); 4.08 (m, 1H); 4.18 (m, 1H); 4.21 (s, 2H); 4.28 (m, 1H); 5.13 (dd, 1H); 5.27 (dd, 1H); 6.25 (d, 1H); 6.33 (d, 1H); 6.97 (m, 4H); 7.25 (m, 5H) ppm.

Example 40

(E/Z)-2-Carboxyethyl-1-cyclopropyl-3-(4-fluorophenyl)-prop-2-en-1-one

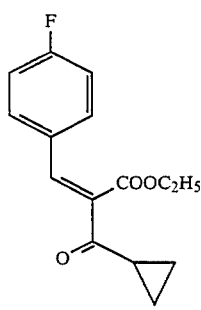

39 g (0.25 mol) of ethyl cyclopropylcarbonylacetate and 31 g (0.25 mol) of 4-fluorobenzaldehyde are initially introduced into 150 ml of dry isopropanol and a mixture of 1.4 ml (14 mmol) of piperidine and 0.83 ml (14.5 mmol) of acetic acid in 20 ml of isopropanol is added. The mixture is stirred for 48 hours at room temperature and concentrated in vacuo, and the residue is distilled in a high vacuum.

B.p. 0.5 mm: 140° C.

Yield: 52.3 g (79.8% of theory)

Example 41

Diethyl 1,4-dihydro-2-cyclopropyl-4-(4-fluorophenyl)-6-isopropyl-pyridine-b 3,5-dicarboxylate

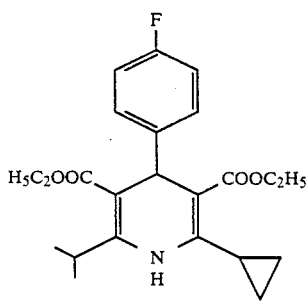

39.3 g (0.15 mol) of the compound from Example 40 and 23.6 g (0.15 mol) of ethyl 3-amino-4-methyl-pent-2-enoate are boiled under reflux overnight in 150 ml of ethylene glycol. After cooling to room temperature, the mixture is extracted several times using ether, the combined ether phases are washed three times with 10% strength hydrochloric acid, and once each with water and saturated sodium hydrogen carbonate solution, dried over magnesium sulphate and concentrated in vacuo. The residue is stirred with petroleum ether/ether, filtered off with suction and dried in a desiccator.

Yield: 22.8 g (37.9% of theory)

$^1$H-NMR (CDCl$_3$): δ=0.65 (m, 2H); 1.03 (m, 2H); 1.15 (m, 13H); 2.78 (m, 1H); 4.15 (m, 4H); 5.03 (s, 1H); 5.72 (s, 1H); 6.90 (m, 2H); 7.22 (m, 2H) ppm.

Example 42

2-Cyclopropyl-4-(4-fluorophenyl)-6-isopropyl-3,5-di(methyl erythro-(E)-3,5-dihydroxy-hept-6-enoat-7-yl)-pyridine

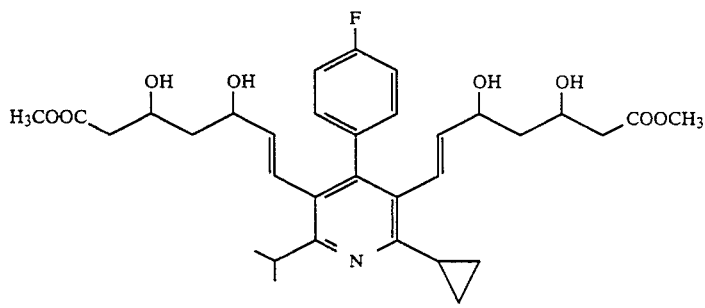

Example 42 was prepared from the compound from Example 41, in analogy to the reactions of Examples 3, 27, 5, 6, 7 and 8.

$^1$H-NMR (CDCl$_3$): δ=0.90 (m, 2H); 1.20 (d, 6H); 1.10–1.60 (m, 6H); 2.25 (m, 1H); 2.43 (m, 4H); 3.25 (m, 1H); 3.73 (s, 6H); 4.08 (m, 2H); 4.30 (m, 2H); 5.22 (dd, 1H); 5.53 (dd, 1H); 6.30 (m, 2H); 6.98 (m, 4H) ppm.

Example 43

Ethyl 3-amino-3-cyclopropyl-acrylate

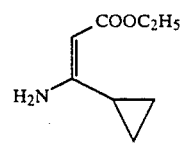

1.1 g of p-toluenesulphonic acid are added to 49.9 g (0.32 mol) of ethyl cyclopropylcarbonylacetate in 200 ml of dry toluene and the mixture is saturated with ammonia gas at room temperature with stirring. After allowing to stand overnight, the mixture is boiled under reflux for 8 hours in a water separator, ammonia gas being continuously introduced. The mixture is allowed to cool overnight and is filtered, and the toluene solution is concentrated in vacuo and removed by distillation in a high vacuum up to 65° C. from unreacted starting material. The substance is subsequently found in the residue. Yield: 11.9 g (24% of theory).

Example 44

Diethyl 1,4-dihydro-2,6-dicyclopropyl-4-(4-fluorophenyl)-pyridine-3,5-dicarboxylate

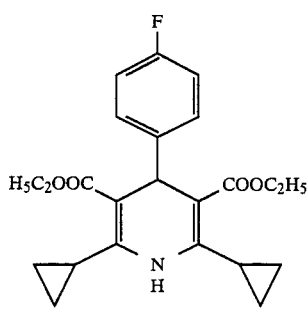

6.2 g (40 mmol) of the compound from Example 43 and 10.5 g (40 mmol) of the compound from Example 40 are dissolved in 100 ml of ethylene glycol and the mixture is boiled to reflux overnight. After cooling to room temperature, the mixture is extracted several times using ether, and the organic phase is washed once each with 10% strength hydrochloric acid, saturated sodium bicarbonate solution and water, dried over magnesium sulphate and concentrated in vacuo.

Yield: 10.4 g (65.1% of theory)

$^1$H-NMR (CDCl$_3$): δ=0.60 (m, 4H); 0.95 (m, 4H); 1.23 (t, 6H); 2.72 (m, 2H); 4.12 (m, 4H); 5.02 (s, 1H); 5.40 (s, 1H); 6.88 (m, 2H); 7.20 (m, 2H) ppm.

Example 45

2,6-Dicyclopropyl-4-(4-fluorophenyl)-3,5-di-(methyl erythro-(E)-3,5-dihydroxy-hept-6-enoat-7-yl)-pyridine

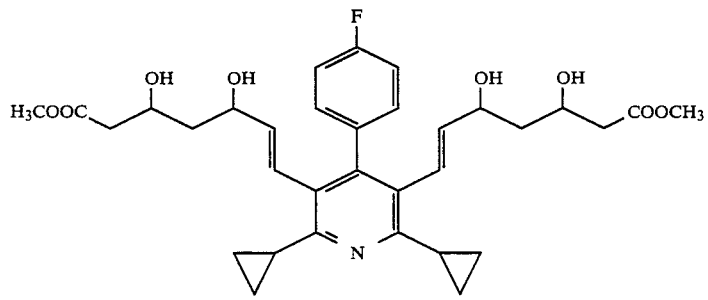

Example 45 was prepared from the compound from Example 44, in analogy to the reactions of Examples 3, 27, 5, 6, 7 and 8.

$^1$H-NMR (CDCl$_3$): δ=0.85 (m, 4H); 1.08 (m, 4H); 1.20–1.60 (m, 4H); 2.20 (m, 2H); 2.43 (m, 4H); 3.70 (s, 6H); 4.12 (m, 2H); 4.33 (m, 2H); 5.52 (dd, 2H); 6.30 (d, 2H); 7.0 (m, 4H) ppm.

Example 46

(E/Z)-4-Carboxyethyl-5-(4-fluoro-3-phenoxyphenyl)-2-methyl-pent-4-en-3-one

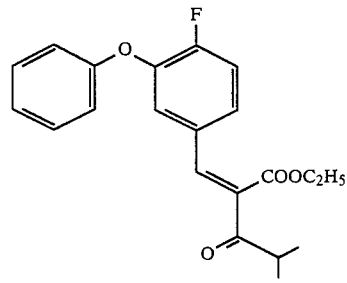

49 g (0.31 mol) of ethyl isobutanoylacetate and 67 g (0.31 mol) of 3-phenoxy-4-fluorobenzaldehyde are initially introduced in 300 ml of isopropanol and a mixture of 1.81 ml (18 mmol) of piperidine and 1.06 ml (18.6 mmol) of acetic acid in 30 ml of isopropanol is added. The mixture is stirred overnight at room temperature, concentrated in vacuo and dried in a high vacuum.

Yield: 110 g (was employed without further purification in Example 47).

Example 47

Diethyl 1,4-dihydro-2,6-diisopropyl-4-(4-fluoro-3-phenoxyphenyl)-pyridine-3,5-dicarboxylate

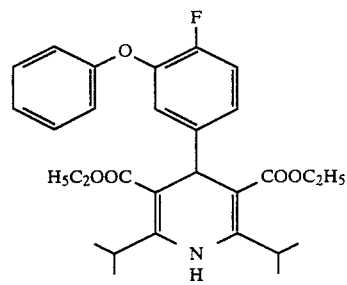

30 g (84.3 mmol) of the compound from Example 46 and 13.2 g (84.3 mmol) of ethyl 3-amino-4-methyl-pent-2-enoate are boiled to reflux overnight in 150 ml of ethanol. The mixture is cooled to 0° C., and the deposited precipitate is filtered off with suction, washed with petroleum ether and dried in a desiccator.

Yield: 18.4 g (44.2% of theory)

$^1$H-NMR (CDCl$_3$): δ=1.05–1.25 (m, 18H); 4.05–4.2 (m, 6H); 4.95 (s, 1H); 6.03 (s, 1H); 6.85–7.1 (m, 6H); 7.3 (m, 2H).

Example 48

2,6-Diisopropyl-4-(4-fluoro-3-phenoxyphenyl)-3,5-di(-methyl erythro-(E)-3,5-dihydroxy-hept-6-enoat-7-yl)pyridine

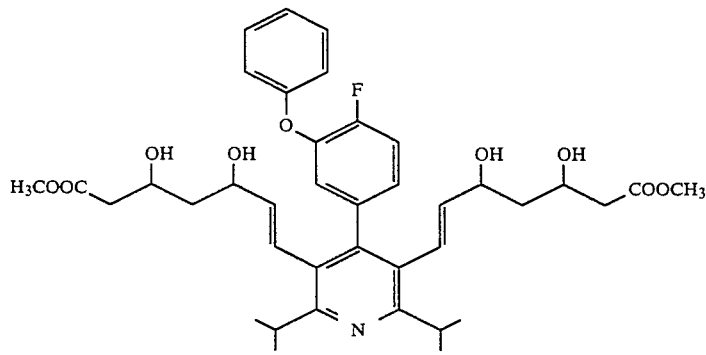

Example 48 was prepared from the compound from Example 47, in analogy to the reactions of Examples 3, 27, 5, 6, 7 and 8.

Example 49

(E/Z)-2-Carboxyethyl-1-(4-fluorophenyl)-3-phenyl-propen-3-one

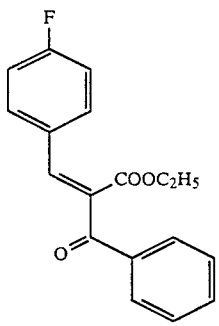

38.4 g (0.2 mol) of ethyl benzoylacetate and 24.8 g (0.2 mol) of 4-fluorobenzaldehyde are dissolved in 200 ml of toluene, 3 ml of piperidine and 3.5 ml of glacial acetic acid are added and the mixture is heated under reflux overnight in a water separator. After cooling to room temperature, the mixture is extracted using saturated sodium hydrogen carbonate solution and water, and the organic phase is dried over magnesium sulphate and concentrated in vacuo. The unreacted starting materials are removed by distillation in a high vacuum and 55.9 g (93% of theory) of crude product are obtained in the distillation residue.

$^1$H-NMR (CDCl$_3$): δ=1.15 (t, 3H); 4.21 (q, 2H); 6.85–7.95 (m, 10H) ppm.

Example 50

Diethyl 1,4-dihydro-4-(4-fluorophenyl)-2-isopropyl-6-phenyl-pyridine-3,5-dicarboxylate

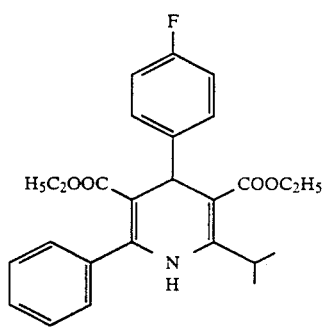

29.8 g (0.1 mol) of the compound from Example 49 and 15.7 g (0.1 mol) of ethyl 3-amino-4-methyl-pent-2-enoate are dissolved in 150 ml of ethylene glycol and boiled to reflux overnight. After concentrating in vacuo, the residue is dissolved in ethyl acetate, washed once each with 10% strength hydrochloric acid, saturated sodium hydrogen carbonate solution and water, dried over magnesium sulphate and concentrated in vacuo. The residue is chromatographed on a column (silica gel 70–230 mesh, using ethyl acetate/petroleum ether 1:5).

Yield: 8.6 g (19.7% of theory)

$^1$H-NMR (CDCl$_3$): δ=0.85 (t, 3H); 1.20 (m, 9H); 3.85 (q, 2H); 4.12 (q, 2H); 4.25 (m, 1H); 5.09 (m, 1H); 5.93 (m, 1H); 6.93 (m, 2H); 7.25–7.50 (m, 7H) ppm.

Example 51

4-(4-Fluorophenyl)-2-isopropyl-6-phenyl-3,5-di-(methyl erythro-(E)-3,5-dihydroxy-hept-6-enoat-7-yl)-pyridine

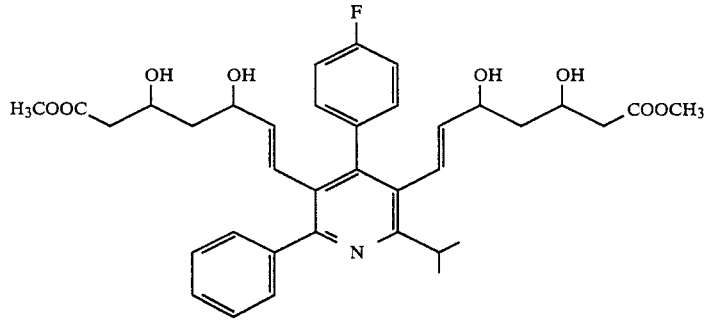

Example 51 was prepared from the compound from Example 50, in analogy to the reactions of Examples 3, 27, 5, 6, 7 and 8.

Example 52

(E/Z)-2-(Carboxy-2-cyanoethyl)-3-cyclohexyl-1-(4-fluorophenyl)-propen-3-one

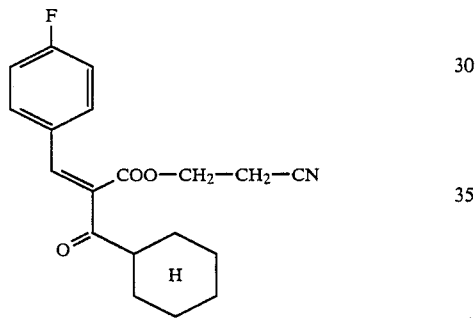

66.9 g (0.3 mol) of 2-cyanoethyl cyclohexylcarbonylacetate and 37.2 g (0.3 mol) of 4-fluorobenzaldehyde were reacted analogously to Example 49. Yield: 56.7 g (57.4% of theory)

Example 53

3-Cyanoethyl 5-ethyl 1,4-dihydro-2-cyclohexyl-4-(4-fluorophenyl)-6-isopropyl-pyridine-3,5-dicarboxylate

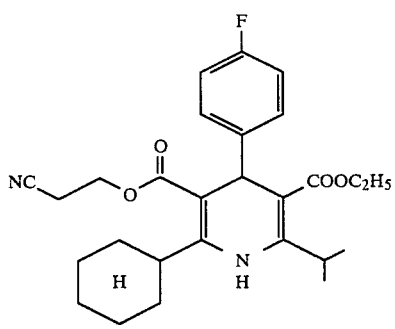

32.9 g (0.1 mol) of the compound from Example 52 and 15.7 g (0.1 mol) of ethyl 3-amino-4-methyl-pent-2-enoate are dissolved in 100 ml of ethanol and boiled to reflux overnight. After concentrating in vacuo, the residue is dissolved in ethyl acetate and washed once each with 10% strength hydrochloric acid, saturated sodium hydrogen carbonate solution and water, the organic phase is dried over magnesium sulphate and concentrated in vacuo. The residue is chromatographed on a column (silica gel 70–230 mesh, using dichloromethane).

Yield: 7.8 g (17.6% of theory)

Example 54

3-Cyanoethyl 5-ethyl 2-cyclohexyl-4-(4-fluorophenyl)-6-isopropyl-pyridine-3,5-dicarboxylate

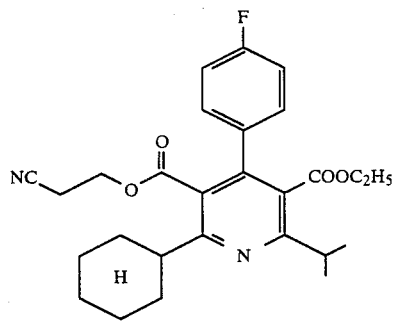

3.53 g (7.55 mmol) of the compound from Example 53 are reacted analogously to Example 3.

Yield: 2.96 g (84% of theory)

$^1$H-NMR (CDCl$_3$): δ=0.98 (t, 3H); 1.33 (m, 10H); 1.82 (m, 6H); 2.35 (t, 2H); 2.69 (m, 1H); 3.10 (m, 1H); 4.02 (q, 2H); 4.15 (t, 2H); 7.08 (m, 2H); 7.28 (m, 2H) ppm.

Example 55

2-Cyclohexyl-3,5-dihydroxymethyl-4-(4-fluorophenyl)-6-isopropyl-pyridine

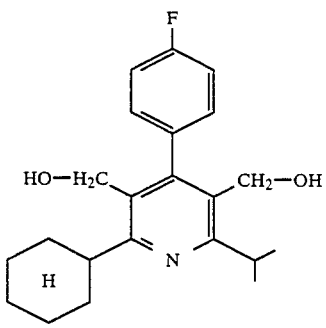

35.7 ml (53.5 mmol) of a 1.5 molar solution of diisobutylaluminum hydride in toluene are added at −78° C. under a nitrogen atmosphere to 2.5 g (5.35 mmol) of the compound from Example 54 dissolved in 50 ml of dry toluene, and the mixture is stirred for 1 hour at −78° C. and overnight at room temperature. 20% strength potassium hydroxide solution is added to the mixture with ice-cooling and it is extracted several times using toluene.

The organic phase is washed with water, dried over magnesium sulphate and concentrated in vacuo.

Yield: 1.64 g (86% of theory)

$^1$H-NMR (CDCl$_3$): δ=1.20–1.50 (m, 4H); 1.35 (d, 6H); 1.70–1.95 (m, 6H); 3.05 (m, 1H); 3.43 (m, 1H); 4.35 (s, 4H); 7.05–7.25 (m, 4H) ppm.

Example 56

2-Cyclohexyl-4-(4-fluorophenyl)-6-isopropyl-3,5-di(-methyl erythro-(E)-3,5-dihydroxy-hept-6-enoat-7-yl)-pyridine

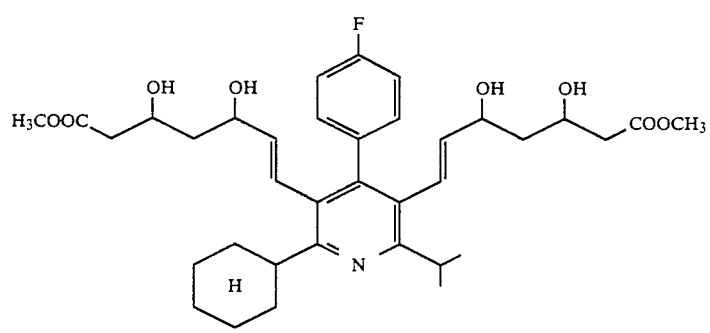

Example 56 was prepared from the compound from Example 55, in analogy to the reactions of Examples 5, 6, 7 and 8.

$^1$H-NMR (CDCl$_3$): δ=1.20–1.85 (m, 20H); 2.41 (m, 4H); 2.90 (m, 1H); 3.28 (m, 1H); 3.70 (s, 6H); 4.08 (m, 2H); 4.30 (m, 2H); 5.25 (dd, 2H); 6.30 (dd, 2H); 7.0 (m, 4H) ppm.

Example 57

(E(2)-3-Ethoxycarbonyl-1-(furane-2-yl)-4-methyl-pent-en-3-on

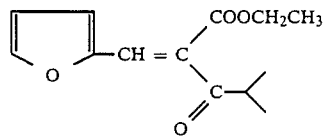

The compound is prepared analogously to Example 1 from furane-2-carbaldehyde.

Yield: 93 % of theory

B.p. 0.5 mbar: 130° C.

Example 58

4-(Furan-2-yl)-[3,5-bis-3,5-dihydroxy-6-methoxycarbonyl-hex-1-enyl]-2,6-diisopropyl-pyridine

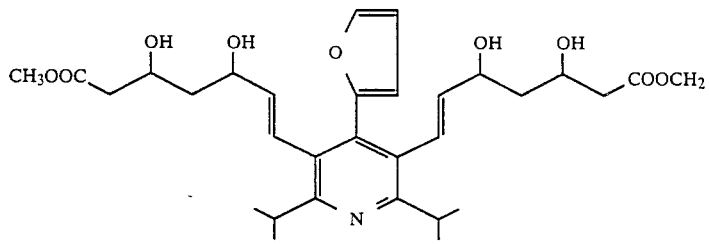

Example 58 was prepared from the compound from Example 57 in analogy to the reactions of Examples 2, 3, 55, 5, 6, 7 and 8.

Colorless crystals of m.p. 106° C.

$^1$H-NMR (CDCl$_3$):δ=1.25 (m, 12H); 1.4–1.65 (m,4H); 2.45 (m, 4H); 2.77 (d, 2H); 3.3 (m, 2H); 3.6 (m, 2H); 3.6 (d, 2H); 3.72 (s, 6H); 4.1 (m, 2H); 4.4 (m, 2H); 5.4 (dd, 2H); 6.12 (m, 1H); 6.4 (m, 1H); 6.5 (d, 2H); 7.45 (M, 1H).

Example 59

(E(2)-3-Ethoxycarbonyl-4-methyl-1(thiophen-2-yl)penten-3-on

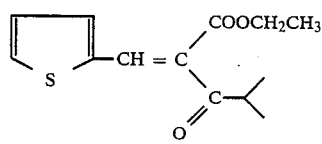

Example 59 was prepared analogously to Example 1 from thiophene-2-carbaldehyde.
Yield: 86 % of theory
B.p. 1.5 mbar: 145° C.

Example 60

3,5-Bis-(3,5-dihydroxy-6-methoxycarbonyl-hex-1-enyl)-2,6 diisopropyl-4-(thiophene-2-yl)-pyridine

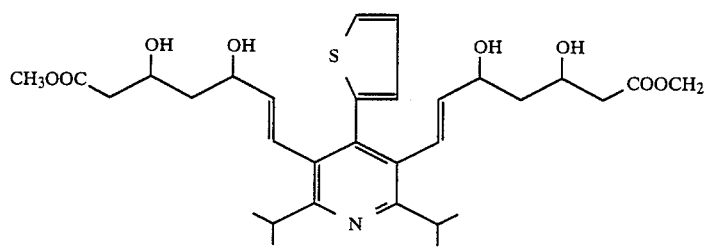

Example 60 was prepared from the compound of Example 59 in analogy to the reactions of Examples 2, 3, 27, 5, 6, 7 and 8.
Colorless crystals of m.p. 62° C.
$^1$H-NMR (CDCl$_3$): δ=1.25 (m, 12H); 1.35–1.6 (m, 4H); 2.45 (m, 4H); 2.6 (s, 2H); 3.3 (m, 2H); 3.5 (d, 2H); 3.72 (s, 6H); 4.1 (m, 2H); 4.35 (m, 2H); 5.48 (dd, 2H); 6.4 (d, 2H); 6.74 (m, 1H); 6.98 (m, 1H); 7.28 (m, 1H).

Example 61

Di-sodium 2,6-diisopropyl-4-phenyl-3,5-di-(erythro-(E)-3,5-dihydroxy-hept-6-enoat-7-yl)-pyridine

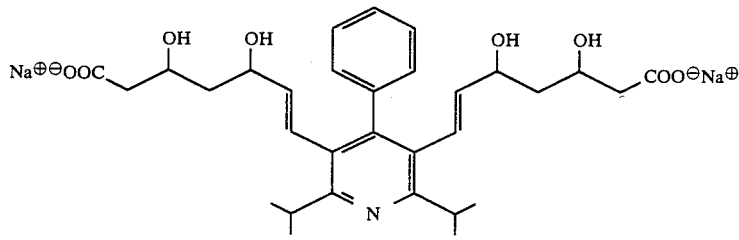

583 mg (1 mmol) of the compound from Example 16 are dissolved in 10 ml of tetrahydrofuran. After addition of 20 ml of 0.1 N NaOH, the mixture is allowed to stand for 1 hour at room temperature is concentrated in vacuo, and the aqueous solution is then lyophilized.
Yield: 605 mg (96.5% of theory).

Use Example

Example 62

The determination of enzyme activity was carried out as modified by G. C. Ness et al., Archives of Biochemistry and Biophysics 197, 493–499 (1979). Male Rico rats (body weight 300–400 g) were treated for 11 days with altromin powdered food, to which 40 g of cholestyramine/kg of food was added. After decapitation, the liver of the animals was taken out and placed on ice. The livers were comminuted and homogenized 3 times in a Potter-Elvejem homogenizer in 3 volumes of 0.1 M saccharose, 0.05M KCl, 0.04M K$_x$H$_y$ phosphate, 0.03M ethylenediaminetetraacetic acid and 0.002M dithiothreitol (SPE) buffer pH 7.2. The homogenizate was subsequently centrifuged for 15 minutes at 15,000* g and the sediment was discarded. The supernatant was sedimented at 100,000 g for 75 minutes. The pellet was taken up in ¼ volumes of SPE-buffer, homogenized again and subsequently centrifuged again at 100,000 g for 60 minutes. The pellet was taken up in 5 times its volume of SPE-buffer, homogenized, and frozen and stored at −78° C. (=enzyme solution).

For testing, the test compounds (or mevinolin as a reference substance) were dissolved in dimethylformamide with the addition of 5% by volume of 1N NaOH and employed in the enzyme test using 10 μin various concentrations. The test was started after 20 minutes preincubation of the compounds with the enzyme at 37° C. The test batch was 0.380 ml and contained 4 μmol of glucose-6-phosphate, 1.1 mg of bovine serum albumin, 2.1 μmol of dithiothreitol, 0.35 μmol of NADP, 1 unit of glucose-6-phosphate dehydrogenase, 35 μmol of K$_x$H$_y$ phosphate pH 7.2, 20 μl of enzyme preparation and 56 nmol of 3-hydroxy-3-methyl-glutaryl coenzyme A (glutaryl-3-$^{14}$C) 100,000 dpm.

The batch was incubated for 60 minutes at 37° C. and the reaction was stopped by addition of 300 μl of 0.24 m HCl. After a post-incubation of 60 minutes at 37° C., the batch was centrifuged and 600 μl of the supernatant were applied to a 0.7×4 cm column filled with Bi-orex$^{(R)}$ 5-chloride 100–200 mesh (anion exchanger). This was washed with 2 ml of distilled water, and 3 ml of aquasol was added to the eluent plus washing water and counted in the LKB scintillation counter. IC$_{50}$ values were determined by intrapolation by plotting the percentage inhibition against the concentration of the compound in the test. To determine the relative inhibitory potency, the $IC_{50}$ value of the reference substance mevinolin was set at 100 and compared with the simultaneously determined $IC_{50}$ value of the test compound.

Example 63

The subchronic action of the disubstituted pyridines on blood cholesterol values of dogs was tested in feeding experiments extending over several weeks. For this, the substance to be investigated was given p.o. once daily in a capsule to healthy beagle dogs together with the feed over a time period of several weeks. In addition, during the entire experimental period, i.e. before, during and after the administration period, the substance cholestyramine (4 g/100 g of feed) to be investigated was mixed with the feed as the gallic acid sequestrant. Twice weekly, venous blood was taken from the dogs and the serum cholesterol was determined enzymatically. The serum cholesterol values during the administration period were compared with the serum cholesterol values before the administration period (controls).

A lowering of the serum cholesterol of about 22.4% thus resulted, e.g., for the Na salt of Example 8 (2,6-diisopropyl 4-(4-fluorophenyl)-3,5-di-(sodium erythro-(E)-3,5-dihydroxy-hept-6-enoat-7-yl)-pyridine) after a 2-week administration of 8 mg/kg p.o. daily.

It will be appreciated that the instant specification and claims are set forth by way of illustration and not limitation, and that various modifications and changes may be made without departing from the spirit and scope of the present invention.

What is claimed is:

1. A compound of the formula

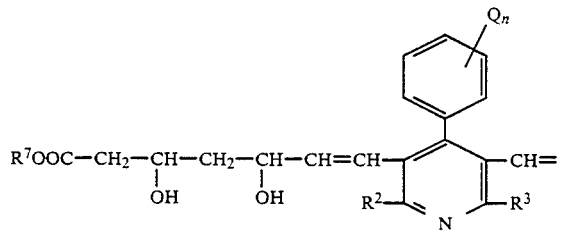

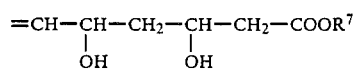

in which
Q stands for F, lower alkyl or phenoxy,
n stands for 1 or 2,
$R^2$ stands for $C_1$-$C_6$ alkyl, $C_3$-$C_8$ cycloalkyl, phenyl or benzyl,
$R^3$ stands for $C_1$-$C_6$ alkyl or $C_3$-$C_8$ cycloalkyl, and
$R^7$ stands for hydrogen, $C_1$-$C_6$ alkyl or an alkali metal cation,
and the stereoisomeric forms which can have the E or Z configuration thereof.

2. A compound according to claim 1 in which $Q_n$ is 4-F.

3. A compound according to claim 1, wherein such compound is 2,6-diisopropyl-4-(4-fluorophenyl)-3,5-di-methyl 3,5-dihydroxy-hept-6-enoat-7-yl)-pyridine of the formula

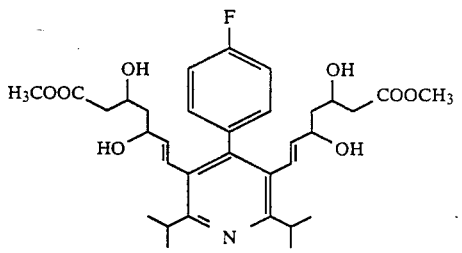

4. A composition for the treatment of lipoproteinaemia and arteriosclerosis which comprises an amount effective therefor of a compound according to claim 1 and a pharmaceutically acceptable diluent.

5. A method of treating lipoproteinaemia and arteriosclerosis which comprises administering to a patient in need thereof an amount effective therefor of a compound according to claim 1.

6. The method according to claim 5, wherein such compound is 2,6-diisopropyl-4-(4-fluorophenyl)-3,5-di-(methyl 3,5-dihydroxy-hept-6-enoat-7-yl)-pyridine.

* * * * *

UNITED STATES PATENT AND TRADEMARK OFFICE
CERTIFICATE OF CORRECTION

PATENT NO. : 4,968,689

DATED : November 6, 1990

INVENTOR(S) : Angerbauer et al.

It is certified that error appears in the above-identified patent and that said Letters Patent is hereby corrected as shown below:

Title Page    [75] Inventors:  Last inventor delete " Thomas Gunter " and substitute -- Gunter Thomas --

Signed and Sealed this

Fifth Day of January, 1993

Attest:

DOUGLAS B. COMER

*Attesting Officer*    *Acting Commissioner of Patents and Trademarks*